(12) United States Patent
Lyon

(10) Patent No.: US 8,480,676 B2
(45) Date of Patent: Jul. 9, 2013

(54) BONE TAMP APPARATUS AND METHOD

(76) Inventor: Thomas R. Lyon, Brooklyn, NY (US)

( * ) Notice: Subject to any disclaimer, the term of this patent is extended or adjusted under 35 U.S.C. 154(b) by 650 days.

(21) Appl. No.: 12/376,780

(22) PCT Filed: Mar. 6, 2007

(86) PCT No.: PCT/US2007/005626
§ 371 (c)(1),
(2), (4) Date: Feb. 6, 2009

(87) PCT Pub. No.: WO2008/020896
PCT Pub. Date: Feb. 21, 2008

(65) Prior Publication Data
US 2010/0191296 A1    Jul. 29, 2010

Related U.S. Application Data

(60) Provisional application No. 60/836,011, filed on Aug. 7, 2006.

(51) Int. Cl.
*A61F 2/46* (2006.01)

(52) U.S. Cl.
USPC ...................................... 606/86 R

(58) Field of Classification Search
USPC .............. 606/86 R, 79, 80, 83–85, 105
See application file for complete search history.

(56) References Cited

U.S. PATENT DOCUMENTS

| | | | | |
|---|---|---|---|---|
| 4,877,020 A | * | 10/1989 | Vich | 606/86 R |
| 4,909,798 A | * | 3/1990 | Fleischhacker et al. | 604/256 |
| 5,197,971 A | * | 3/1993 | Bonutti | 606/192 |
| 5,354,302 A | * | 10/1994 | Ko | 606/104 |
| 5,667,513 A | * | 9/1997 | Torrie et al. | 606/104 |
| 6,143,030 A | * | 11/2000 | Schroder | 623/16.11 |
| 6,241,734 B1 | * | 6/2001 | Scribner et al. | 606/93 |
| 6,613,018 B2 | | 9/2003 | Bagga et al. | |
| 6,613,054 B2 | | 9/2003 | Scribner | |
| 6,860,889 B2 | * | 3/2005 | Bonati et al. | 606/104 |
| 7,066,942 B2 | | 6/2006 | Treace | |
| 2002/0032447 A1 | * | 3/2002 | Weikel et al. | 606/86 |
| 2002/0099385 A1 | | 7/2002 | Ralph | |
| 2003/0109883 A1 | * | 6/2003 | Matsuzaki et al. | 606/86 |
| 2004/0010260 A1 | | 1/2004 | Scribner | |
| 2004/0092946 A1 | | 5/2004 | Bagga et al. | |
| 2005/0070898 A1 | * | 3/2005 | Jones | 606/53 |
| 2005/0182414 A1 | | 8/2005 | Manzi et al. | |
| 2006/0116689 A1 | | 6/2006 | Albans | |

FOREIGN PATENT DOCUMENTS

| DE | 3922044 A1 | 2/1991 |
|---|---|---|
| DE | 3922044 A1 | 7/1991 |

* cited by examiner

*Primary Examiner* — Kevin T Truong
*Assistant Examiner* — Zade Coley
(74) *Attorney, Agent, or Firm* — Harold G. Furlow, Esq

(57) ABSTRACT

A tamping apparatus is described that includes a cannula that has a tubular wall that includes a distal end portion that defines a tamping face. The cannula defines a longitudinally aligned aperture or lumen that provides access for an insert and the injection of treatment materials such as a bone graft. The distal end portion of the cannula can also include a plurality of movable elements that can be a part of or connected to the tubular wall. The tamp apparatus can also include a cannula or stylet that can be moved within aperture of cannula and is employed to move elements between the first position and second position of tamp apparatus.

23 Claims, 16 Drawing Sheets

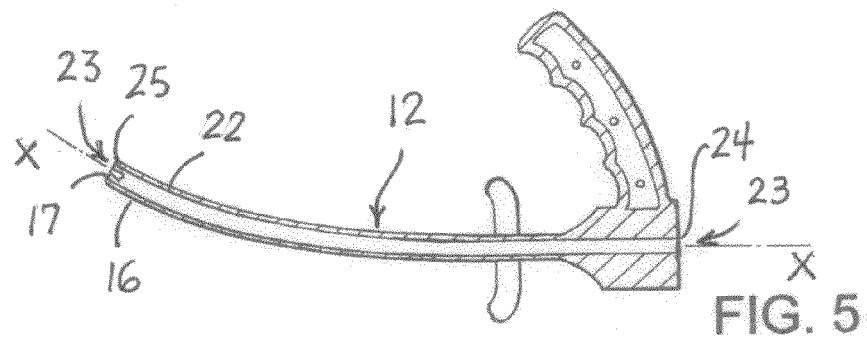
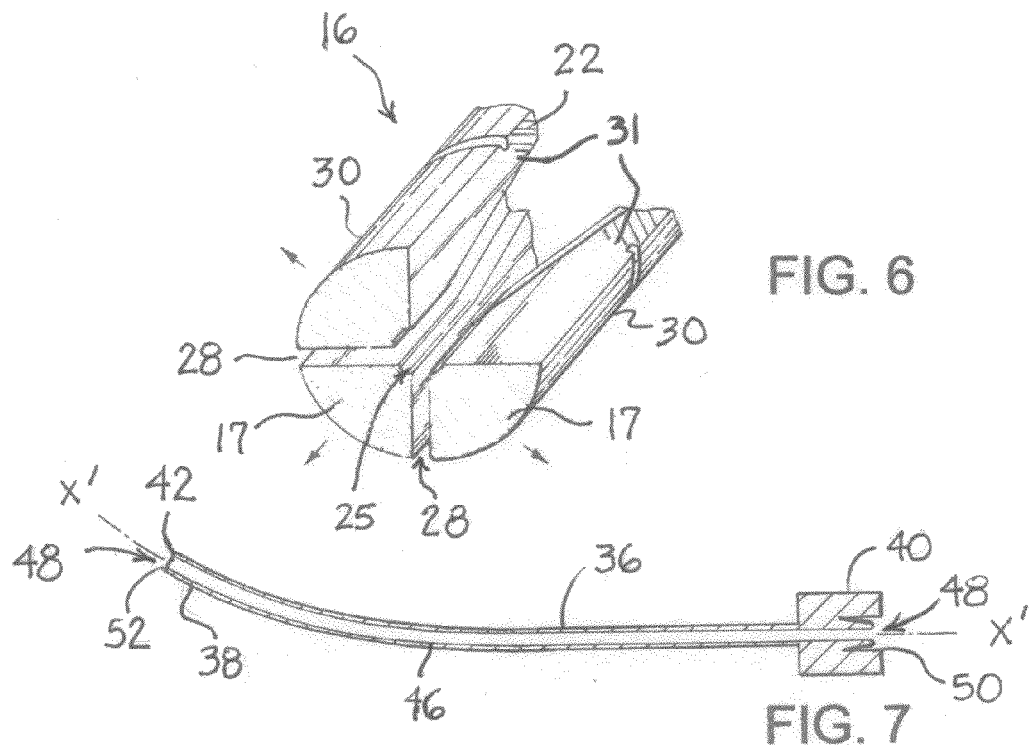
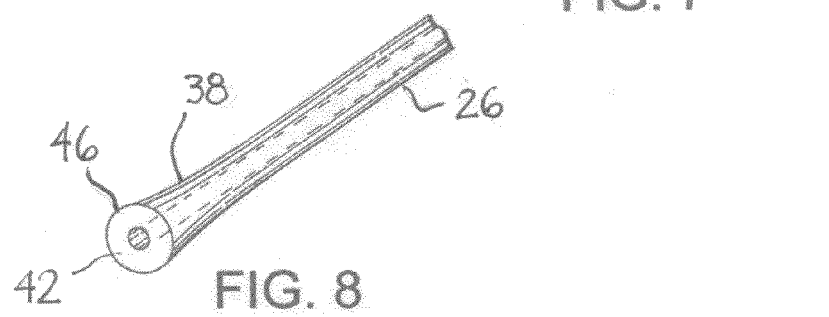

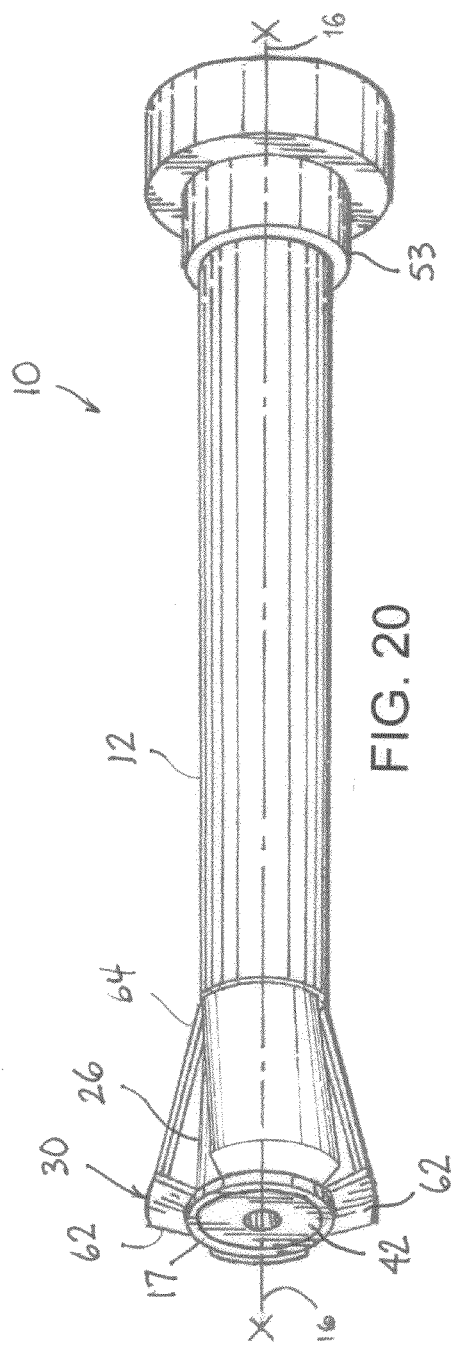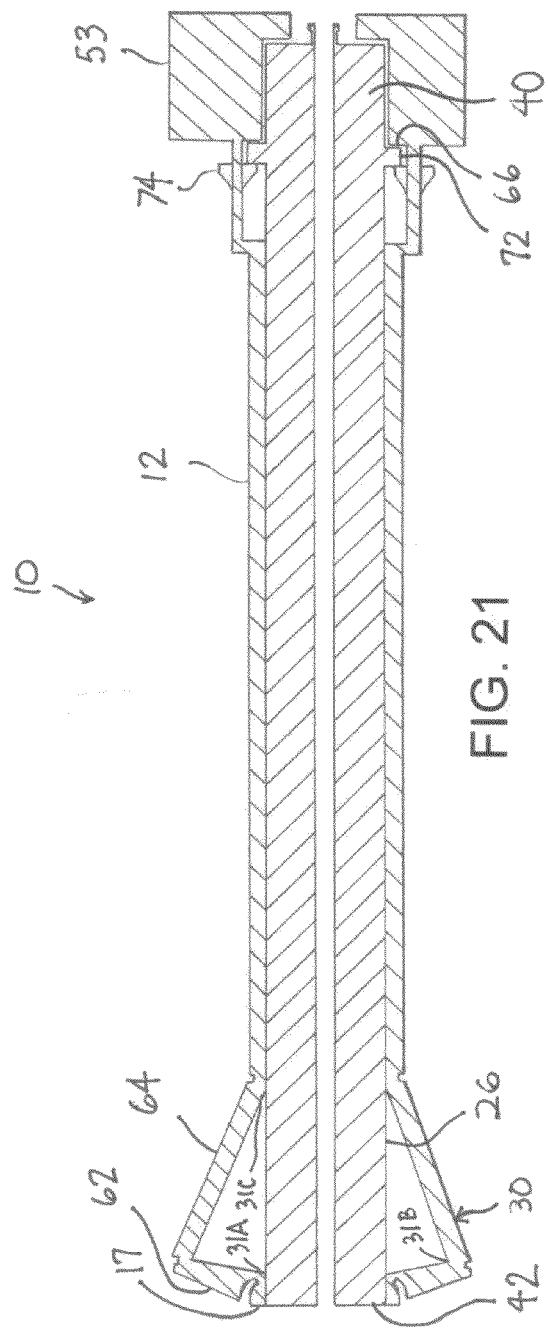

BONE TAMP APPARATUS AND METHOD

CROSS-REFERENCE TO RELATED APPLICATION

This application claims priority to provisional patent application 60/836,011 filed Aug. 7, 2006, the disclosure of which is incorporated by reference herein in its entirety.

BACKGROUND OF THE INVENTION

1. Field of the Invention

The present invention relates to surgical tamps and more specifically to a bone tamp apparatus.

2. Description of the Related Art

Bone tamps provide surgeons a valuable option for the repair of compression bone fractures. The tibial plateau, as one example, is vulnerable to being fractured and depressed due to varus or valgus stress and/or axial compression. Bone tamps are used to reposition the fractured and displaced bone into a natural position. Prior art bone tamps are typically simple solid straight instruments that have a cylindrical shape and a distal face or tamping surface with a fixed quantity of surface area for the displacing of bone tissue. The tamping surfaces of prior art bone tamps are solid and have flat disk type shapes without openings or breaks in the tamping surfaces.

In one current surgical procedure as an example, access to the tibia is created by making a surgical incision in a generally anterior and medial position on the proximal aspect of the tibia, below the level of the tibial plateau fracture as shown in FIG. 1 (prior art). An opening is then created in the hard, outer, cortical bone in line with this incision in order to provide access for a bone tamp. This opening in the cortical bone is typically created by making multiple drill holes in a circular shape and then connecting these holes through the use of an osteotome and a mallet. After removing this "cortical window" in the bone, a tamp is inserted through the window into the soft, inner cancellous bone where it is then positioned for treating the tibia fracture. A mallet is used to tap the proximal terminal end and drive the distal tamping face of the tamp into the fracture. The tamp repositions the displaced bone material into a natural position.

When the tamping of the displaced bone material is completed, the tamp is withdrawn. The path taken by tamp to return the displaced bone to the natural position leaves a void in the bone that is then backfilled using a bone graft or bone graft substitute such as various, commercially available bone cements. The back filling procedure places the bone graft into the void by injecting the material through a large bore needle or cannula. Tamps may also be used to compress the backfilled bone graft to ensure the structural integrity of the graft. The term bone graft as defined herein includes a bone graft, bone graft substitute, bone cement or any another material approved for use as a bone graft. The term tamping surface as defined herein is the distal terminal end or face of the tamp that directly contacts the cancellous bone as described above to displace that bone and/or compress the bone graft.

The simple prior art bone tamp is limited in its ability to perform additional functions during a surgical procedure. For example, the tamp requires a large bone window and skin incision. This causes significant bleeding and soft tissue trauma. The placement of the tamp directly below the fracture site can also be difficult and typically requires several trial and error attempts each of which leaves a path of bone void which needs to be backfilled at the end of the procedure. The application of the prior art tamp to many common fractures can also require an excessive amount of time due to the relatively small surface of the face of the tamp relative to the wider surface of the fracture. Effective backfilling can also be compromised by the fact that the prior art tamps require a two step process in which the tamp is removed and then the bone graft is injected into the void. Problems occur because upon the removal of the tamp from the bone, blood begins to accumulate in the void from the tamp that prevents an optimal graft integration with the native bone.

While cannulas have expandable structures for different functions, such as those in U.S. Pat. No. 6,632,197 to Lyon that, is incorporated herein by reference and made a part of this disclosure, heretofore bone tamps have neither had apertures aligned with the longitudinal axis or structures that increase the tamping surface area. Tamps have not had apertures for receiving a guide wire which can perform functions such as the scouting out and aligning of the ultimate trajectory of the tamp as welt as the introduction of backfill.

The repair of certain bone fractures, such as those of the tibial plateau can benefit from a tamp apparatus that is not solely limited to tamping. A tamp apparatus is needed that combines a tamp and a cannula that defines a through hole or aperture that is aligned with a longitudinal axis of the tamp. The aperture advantageously provides a passageway for a guide wire such that the tamp apparatus can be slid over an accurately pre-positioned guide wire that is placed beneath the depressed fragment of bone. The guide wire can then be used to direct the tamp to the desired point and angle for application. In addition, the aperture allows for the subsequent injection of bone graft through the aperture of the cannula as the tamp is withdrawn from the fracture site. Further, a tamp apparatus is needed that has a narrow cross-section that can be selectively expanded to increase the tamping surface.

SUMMARY OF THE INVENTION

A tamp apparatus is described for use in surgical operations that comprises a cannula that has a tubular wall that has a distal end portion and a proximal end portion. The distal end portion includes a distal terminal end and the proximal end portion includes a proximal terminal end. The tubular wall of the cannula defines an aperture. The aperture extends from a first opening defined in the proximal terminal end to a second opening defined in the distal terminal end. A tamping surface for displacing bone is defined by the distal terminal end of the distal end portion of cannula between an outside diameter of the tubular wall of distal terminal end and an outside diameter of the second opening. The first opening has a first diameter and the second opening has a second diameter such that the diameter of the first opening is larger than the diameter of the second opening. The distal end portion and proximal end portion of the cannula define a central longitudinal axis.

The distal end portion includes a plurality of slots defined in the tubular wall and the slots define a plurality of elements. The elements are movable between a first position aligned with the longitudinal axis and a second position oblique to the longitudinal axis. The elements are cantilevered portions of the tubular wall that reduce the diameter of the second opening of the aperture in the first position of the tamp apparatus. The elements have terminal ends that define a tamping face of the cannula. The elements include at least one hinge. A displacing force rotates the elements about their respective hinges from the first position aligned with the longitudinal axis to the second position oblique to the longitudinal axis. The elements include a retention mechanism or elasticity that biases the elements to the first position.

The tamp apparatus can further includes a stylet and the stylet has a tubular wall that includes a distal end portion, a central section and a proximal end portion. The distal end portion includes a distal terminal end and the proximal end portion includes a proximal terminal end. An aperture is defined by the tubular wall of the stylet. The aperture extends from a first opening defined in the proximal terminal end to a second opening defined in the distal terminal end. At least the tubular wail of the distal end portion and the central section of the stylet are positionable in the aperture of the cannula. The cannula and the stylet are connectable together into an integrated assembly.

A surgical tamp is described that comprises a tamp apparatus. The tamp apparatus includes a cannula. The cannula has a tubular wall that has a distal end portion and a proximal end portion. The distal end portion has a distal terminal end and the proximal end portion has a proximal terminal end. An aperture is defined by the tubular wail of the cannula that extends from a first opening defined in the proximal terminal end to a second opening defined in the distal terminal end. A first position of the tamp apparatus defines a first tamping surface area and a second position of the tamp apparatus defines a second tamping surface area. The second tamping surface area has a greater tamping surface area than the first tamping surface area.

The surgical tamp can further include an insert. The insert has a proximal end portion and a distal end portion. The insert is positionable in the aperture of the cannula. The distal end portion of the insert includes a tamping face that increases the tamping surface area of the tamp apparatus in the second position. The cannula can include a plurality of movable elements that have tamping faces. The elements are approximately aligned with the aperture in the first position and in the second position the tamping faces deploy to increase the tamping surface area of the tamp apparatus. The surgical tamp can further include at least one stylet that has a tamping face. The stylet is positionable in the aperture and the stylet deploys the tamping faces of the elements from the first position to the second position. The tamping face of the stylet and the tamping faces of the elements increase the tamping surface area of the tamp apparatus in the second position.

A method of treating a bone fracture using a tamp apparatus comprising the steps of introducing a guide wire through a pre-existing incision in a cortex of a bone and positioning a distal end of the guide wire in proximity to a bone fracture. Coupling a longitudinally aligned lumen of the tamp apparatus to the guide wire and positioning a distally directed tamping face of the tamping apparatus for treating the fracture. Treating the fracture using the tamping fate to displace the fractured bone material to an approximately natural position.

The method can further comprise removing the guide wire from the tamp apparatus when the tamp apparatus is positioned for treating the fracture. The method can also further comprise selectively positioning the tamp apparatus between a first position with a first tamping face surface area and a second position with a second tamping face surface area. The second tamping face surface area is greater than the first tamping face surface area. The method further comprising injecting bone graft material through a distal opening of the lumen of the tamp apparatus to further treat the displaced fractured bone.

BRIEF DESCRIPTION OF THE DRAWINGS

Preferred embodiments of the invention are described below with reference to the drawings, wherein like numerals are used to refer to the same or similar elements.

FIG. 5 is a side cross-sectional view of the cannula of FIG. 4 taken along lines 5-5.

FIG. 6 is a front perspective view of a distal end portion of the cannula of FIG. 4 that has one of the four elements removed;

FIG. 7 is a side cross-sectional view of the stylet of the tamp apparatus of FIG. 4 taken along lines 7-7;

FIG. 8 is a front and side perspective view of a distal end portion of a second embodiment of the stylet of FIG. 4 wherein the distal end portion has a taper that increases the diameter of a terminal end of the stylet;

FIG. 20 is a front perspective view of the tamp apparatus of FIG. 18 in a second position that shows the elements rotated to form a tamping surface;

FIG. 21 is a side cross-sectional view of the tamp apparatus of FIG. 20 along lines 21-21 in the second position that shows the elements flexed to a second position;

DETAILED DESCRIPTION OF THE INVENTION

Figure 1:
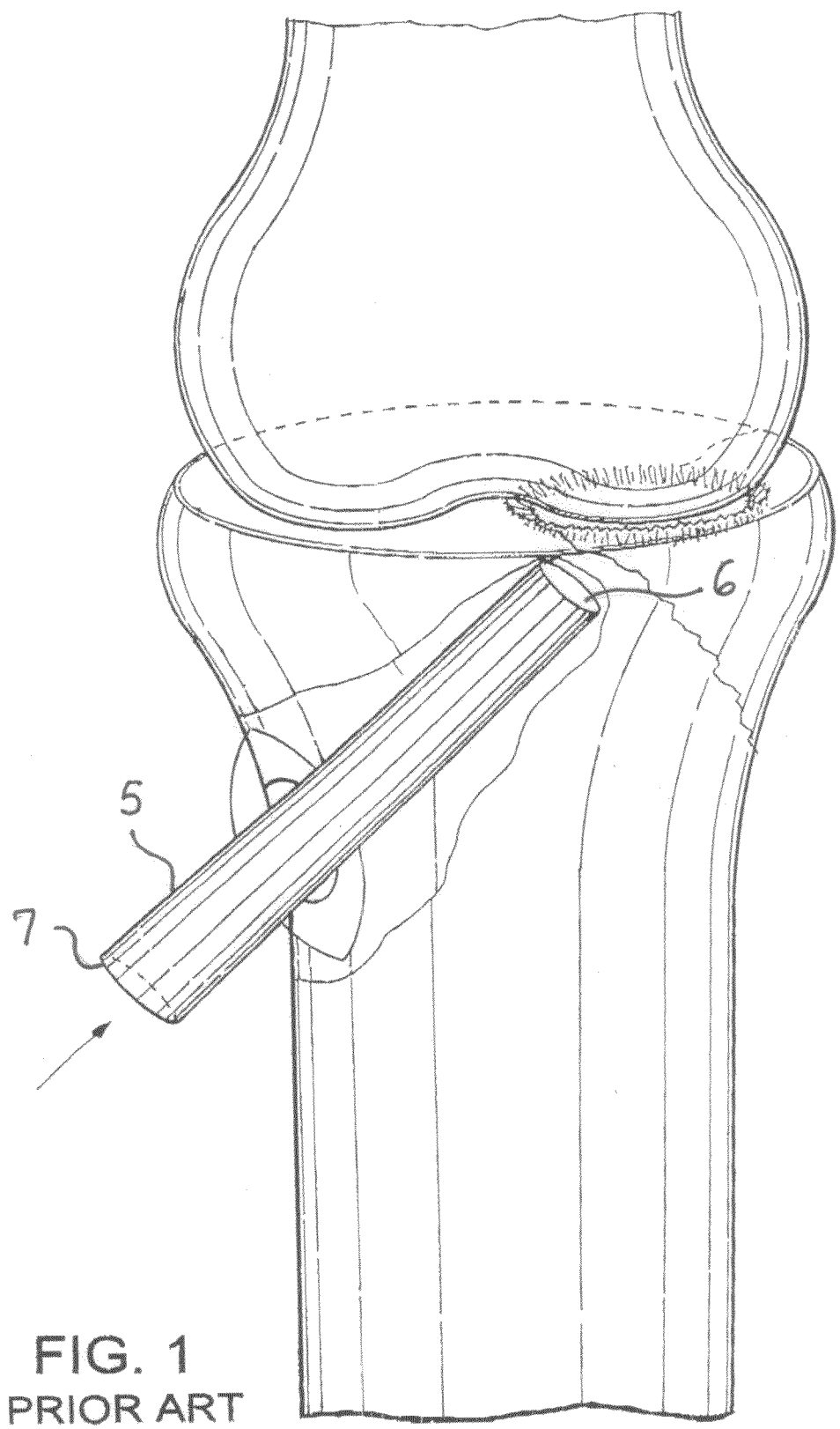
FIG. 1 is a side perspective view of a tibial plateau fracture being treated with a prior art tamp.

Referring to the drawings and initially to FIG. 1, a prior art tamp 5 is shown that is a simple solid straight cylindrically shaped rod. Tamp 5 is provided with access to the vicinity of an anterior portion of the tibial plateau by a surgical incision. A distal terminal end 6 of tamp 5 is positioned on the tibia and a proximal terminal end 7 of tamp 5 is struck to displace the compressed bone structure. Once the depressed portion of the tibial plateau has been elevated to approximate the original tibial plateau surface, tamp 5 is withdrawn. A separate device, such as a stylet or syringe (not shown) is then positioned into the incision to supply a bone graft or another material such as a bone graft substitute or cement to fill the displaced bone of the tibia. Tamp 5 is then used to compress the backfilled bone graft.

Figure 2:
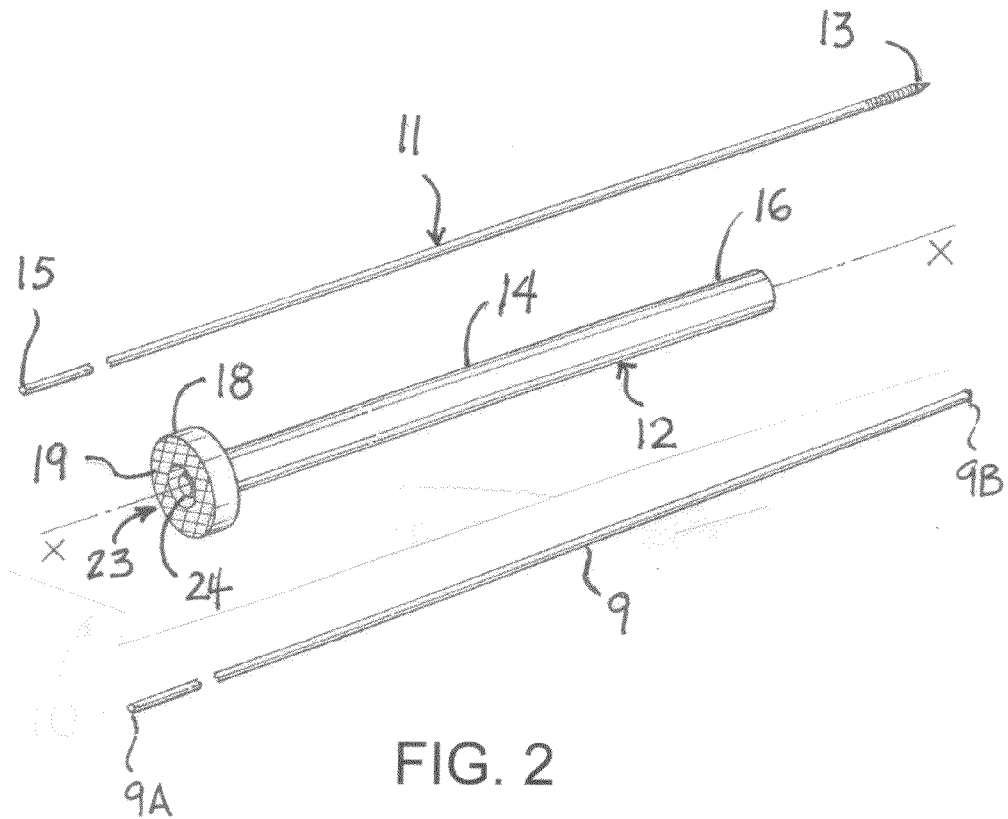
FIG. 2 is a side and rear perspective view of one preferred embodiment of a bone tamp apparatus that includes a cannula, a guide wire and an insert constructed in accordance with the present disclosure.

As shown in FIG. 2, tamp apparatus 10 in this preferred embodiment is a cylindrical shaped tubular cannula 12 that includes a central section 14, a distal end portion 16 and a proximal end portion 18. Cannula 12 defines a central longitudinal axis-X between distal end portion 16 and proximal end portion 18. Distal end portion 16 has a terminal end or tamping face 17. Proximal end portion 18 has a terminal end or base 19. Cannula 12 is shown as having a straight shape, but it is understood that cannula 12 can also have an arcuate shape. Tamp apparatus 10 can selectively include an insert 9 and/or a guide wire 11.

Proximal end portion 18 preferably has a larger diameter than tubular wall 22 of central section 14 and distal end portion 16. The larger diameter of proximal end portion 18 provides a larger proximally directed surface of base 19 that provides a larger target or striking area. Base 19 has a flat surface that is suitable for being tapped or struck by a mallet, for example.

Insert 9 is a solid cylindrical stylet that has a center section that connects a proximal end portion 9A and a distal end portion 9B. Proximal end portion 9A preferably connects to proximal end portion 18 of cannula 12 to form a single integrated assembly that transfers a force applied to cannula 12 and/or insert 9 along the longitudinal axis. Distal end portion 9B includes a distally directed terminal end or tamping face that combines with the tamping face 17 of cannula 12 to increase the tamping surface of tamp apparatus 10.

Guide wire 11 has a distal end 13 and a proximal end 15. In this preferred embodiment, guide wire 11 is preferably a straight substantially rigid cylindrically shaped wire, but it is understood that guide wire 11 can have alternate shapes, such as arcuate, or be at least partially flexible.

Figure 3:
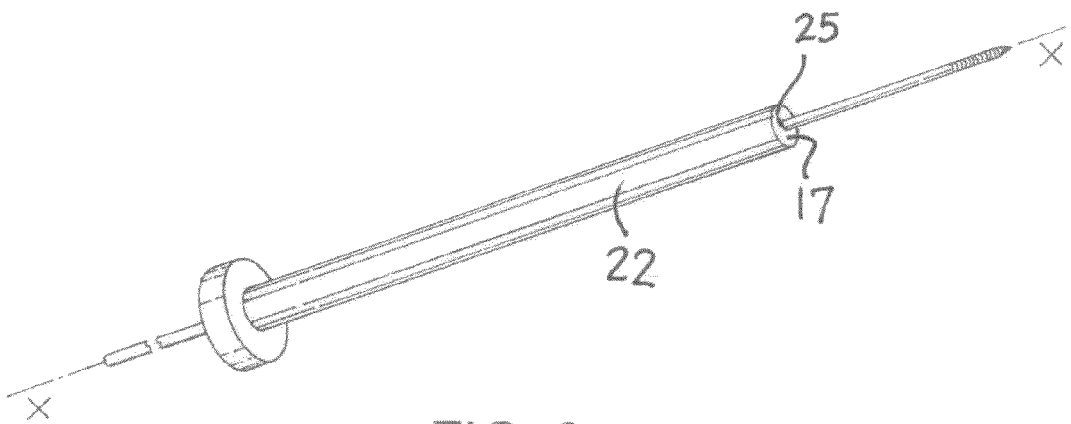
FIG. 3 is a side and front perspective view of the bone tamp apparatus and guide wire of FIG. 2 with the guide wire positioned through an aperture in a cannula of the tamp apparatus.

Referring now to FIGS. 2 and 3, cannula 12 has a tubular wall 22 that defines an aperture 23 that is aligned with the longitudinal axis-X. In this preferred embodiment, cannula 12 is a fluid tight conduit or lumen that extends between a first opening 24 in base 19 and a second opening 25 defined in face 17. Aperture 23 has a diameter that is at least slightly larger than the diameter of guide wire 11.

In this preferred embodiment, base 19 defines a recessed or hollowed out area that has a recessed surface below or distal to base 19. The recessed surface defines first opening 24 that can include a standard interface such as a leur lock, for example, that can connect with a syringe or another surgical instrument.

Second opening 25 of aperture 23 has a diameter that is preferably less than a diameter of first opening 24. The relatively small and/or decreased diameter of aperture 23 at, second opening 25 advantageously increases the tamping surface of face 17. The diameter of second opening 25 is at least sufficient to define a passageway for guide wire 11 and/or the injection of bone material.

Insert 9 is removably positionable into aperture 23 through first opening 24. When insert 9 is fully positioned into aperture 23, tamp apparatus 10 is in a second position wherein distal end portion 9B tamping face defines an additional portion of the tamping surface of tamp apparatus 10 in combination with tamping face 17. Insert 9 can selectively provide a close fitting relationship and/or sealing interface with tamping face 17 and/or aperture 25. Insert 9 is shown as a solid cylindrical shall, but it is understood that insert 9 could have a variety of shapes depending upon the intended application.

Guide wire 11 can be inserted into aperture 23 and rotated about the longitudinal axis-X while positioned in cannula 12. Similarly, when guide wire. 11 is positioned in aperture 23, cannula 12 is movable relative to guide wire 11. In this preferred embodiment, the diameter of aperture 23 is decreased in distal end portion 16 by a taper of the inner surface of tubular wall 22 that decreases aperture 23 to the reduced second diameter at opening 25 in face 17. Tamping face 17 is shown as annular with a surface that is flat and perpendicular to the longitudinal axis-X. It is understood that tamping face 17 can have a variety of shapes depending upon the desired application of tamp-apparatus 10 to include, for example, convex, faceted, angled from the perpendicular to the longitudinal axis or combinations thereof to further improve the application of tamping face 17.

Figure 4:
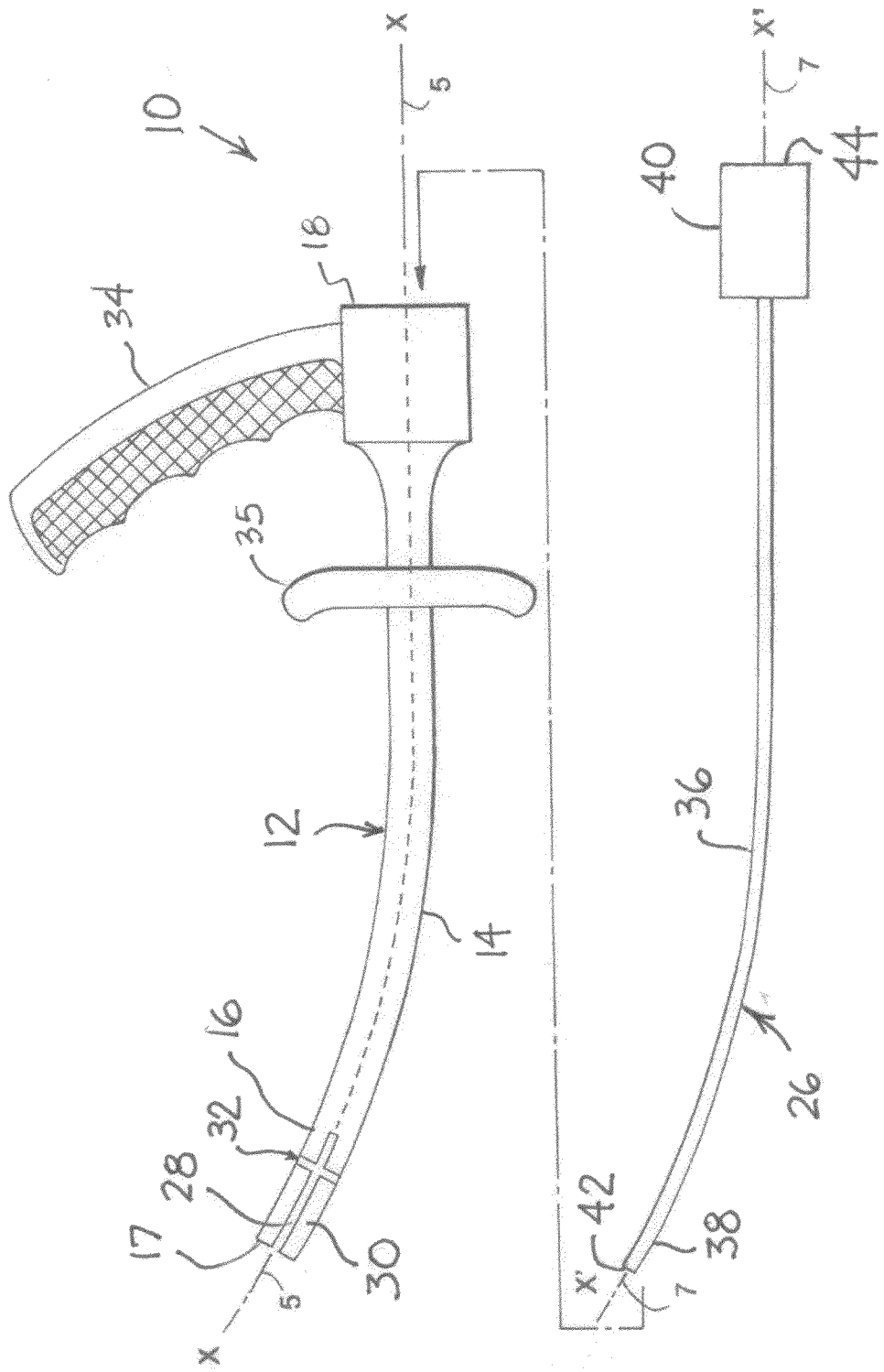
FIG. 4 is a side view of a second embodiment of the tamp apparatus of FIG. 2 in a first position, the tamp apparatus includes a stylet and a cannula constructed in accordance with the present disclosure.

As shown in FIG. 4, bone tamp apparatus 10 in a second preferred embodiment includes a cannula 12 and a stylet 26. Cannula 12 and stylet 26 are separate components that can be connected together to form a single integrated assembly. Cannula 12 is shown in a first position for penetration and/or passing through a body wall and into a portion of a body such as a joint and/or an anatomical cavity. Stylet 26 is a second cannula and defines a central longitudinal axis-X'. Cannula 12 and stylet 26 are shown as being arcuate and defining an arcuate longitudinal axis-X, but it is understood that cannula 12 and stylet 26 can have a straight shape.

Referring now to FIGS. 4 and 5, in this preferred embodiment distal end portion 16 of cannula 12 defines a plurality of slots 28 that extend in a proximal direction from face 17 for a predetermined distance to a proximal terminal end. Slots 28 separate a plurality of cantilevered elements 30 in tubular wall 22 of distal end portion 16. Slots 28 can be in fluid communication with aperture 23 or include seals that preclude fluid communication from the environment external to tubular wall 22 to aperture 23 in the first position of tamp apparatus 10.

Slots 28 are preferably aligned with the longitudinal axis-X. The proximal terminal ends of slots 28 approximately define the proximal terminal ends of elements 30. A notch 32 is defined in tubular wall 22 in proximity to the proximal terminal end of each element 30. In the first position of tamp apparatus 10, elements 30 extend distally and are approximately aligned with the longitudinal axis-X.

Cannula 12 can include a first handle 34 and/or a second handle 35 that can assist in the manipulation of tamp apparatus 10 during surgical procedures. Handles 34 and 35 can also perform other functions such as assisting in the connecting of cannula 12 and stylet 26 into an integrated assembly.

As shown in FIGS. 5 and 6, in this one preferred embodiment of tamp apparatus 10 distal end portion 16 of cannula 12 has four longitudinally aligned slots 28 that separate tubular wall 22 into four cantilevered elements 30. One of the four elements 30 is removed to show the inner surfaces of tubular wall 22 of the remaining three elements 30. Face or terminal end 17 defines second opening 25 and includes the distal ends of each element 30 that define the tamping surface for cannula 12.

Second opening 25 in face 17 has a diameter that is preferably less than the diameter of first opening 24 of aperture 23. In this preferred embodiment, the diameter of aperture 23 is narrowed by a distally directed taper of the inner surface of tubular wall 22 that decreases the diameter of aperture 23 to a reduced second diameter at opening 25 in face 17. This tapered decrease in the diameter of the inner surface of the tubular wall 22 of elements 30 advantageously provides an increase in the tamping surface of face 17.

Tubular wall 22 includes a hinge 3 for the rotation of elements 30 between the first position and a second position of tamp apparatus 10. In this preferred embodiment, hinge 31 is a flexible hinge positioned in proximity to the proximal terminal end of each element 30 and/or notch 32. Tubular wall 22 has material characteristics that accommodate the rotational movement of elements 30 between the first position and the second position of tamp apparatus 10. Hinge 31 can also be a mechanical joint and or have the configuration of a pivot, for example. Hinge 31 is preferably biased to the first position of tamp apparatus 10.

Referring now to FIGS. 4, 5 and 7, stylet 26 is a second cannula that includes a central section 36, a distal end portion 38 and a proximal end portion 40. Distal end portion 38 has a terminal free end or face 42 that is a tamping surface of stylet 26. Proximal end portion 40 has a terminal free end or base 44.

Stylet 26 has a tubular wall 46 that defines an aperture 48 that is in fluid communication with a first opening 50 defined in terminal end or base 42 and a second opening 52 defined in terminal end or face 42. Tubular wall 46 is a fluid tight conduit between openings 50 and 52. The diameter of aperture 48 is at least sufficient to define a passageway for guide wire 11 and/or the injection of bone material. Stylet 26 is approximately rigid along the longitudinal axis in that it directly transfers axially directed forces.

In this preferred embodiment aperture 23 has a diameter that is sufficient to receive at least distal end portion 38 and central section 36. Cannula 12 and stylet 26 preferably have corresponding arcuate shaped distal end portions 16, 38 and central sections 14, 36, respectively such that when stylet 26 axis-X' is approximately aligned with cannula axis-X, aperture 23 of cannula 12 can receive at least distal end portion 38 and central section 36 of stylet 26 through first opening 24.

Distal end portion 38 and face 42 of stylet 26 can vary in geometry depending upon the desired application of tamp apparatus 10. Proximal end portion 40 of stylet 26 includes first opening 50 that can also define a standard interface such as leer lock, for example, for use with additional surgical instruments such as a syringe.

Referring now to FIG. 8, in one preferred embodiment of stylet 26, distal end portion 38 the outside diameter of tubular wall 46 has a distally increasing taper. The central section 36 of tubular wall 46 has a first outside diameter and distal end portion 38 of tubular wall 46 has a second outside diameter that is greater than the first outside diameter. The taper of distal end portion 38 increases the outside diameter of tubular wall 46 and preferably reaches a maximum diameter in proximity to face 42.

Figure 9:
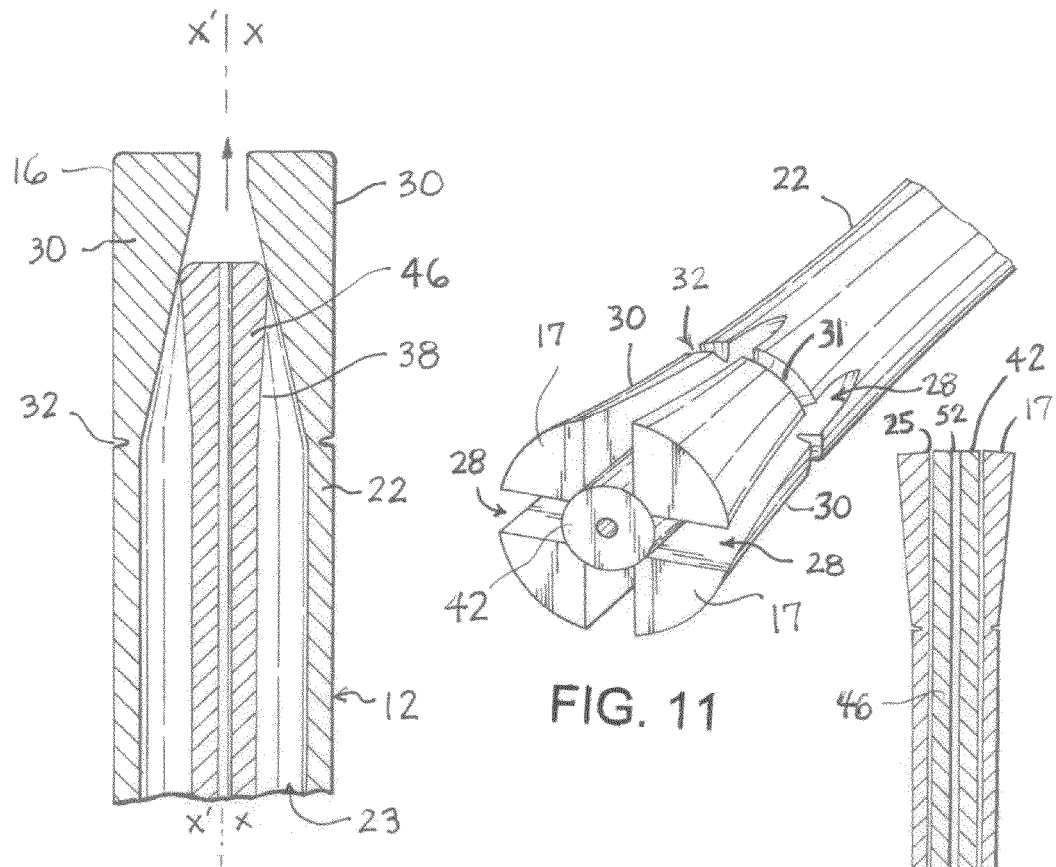
FIG. 9 is a close up of the side cross-sectional view of the stylet of FIG. 8 positioned in the aperture and in direct contact with the elements of the cannula of FIG. 5.

Referring now to FIG. 9, distal end portion 38 of stylet 26 has moved distally into direct contact with the tapered inner surfaces of elements 30 of tubular wall 22 that decrease the diameter of aperture 23. In this preferred embodiment, distal end portion 38 of stylet 26 has a taper that increases the outside diameter of tubular wall 46 in the distal direction. Elements 30 are in the first position prior to deploying. Notches 32 are defined in tubular wall 22.

Figure 10:
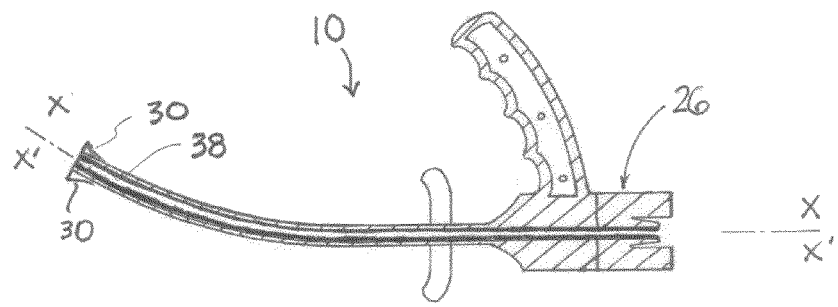
FIG. 10 is a side cross-sectional view of the cannula and stylet of FIG. 4 in a second position of the tamp apparatus.
Figure 11:
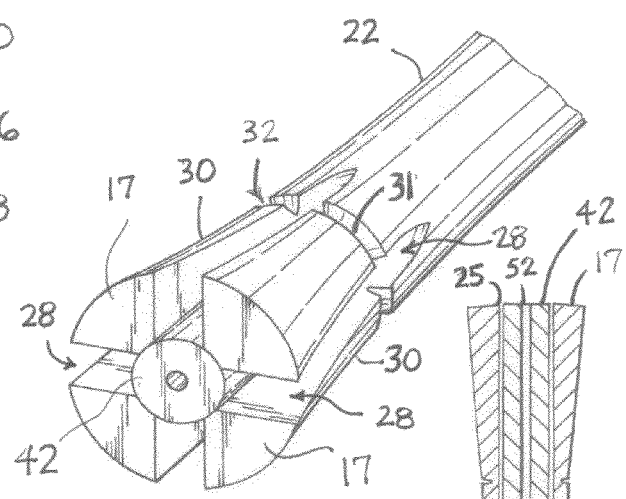
FIG. 11 is a perspective view of the distal end portions of the cannula and stylet of the tamp apparatus of FIG. 4 in a second position with the stylet and expanded elements defining an expanded tamping surface.

As shown in FIGS. 10 and 11, as stylet 26 continues to move in the distal direction, distal end portion 38 deploys elements 30 by displacing elements 30 from the first position aligned with the longitudinal axis-X to a second or deployed position of tamp apparatus 10 wherein elements 30 are positioned at an oblique angle to the longitudinal axis-X. Oblique as defined herein is transverse to or angled from the longitudinal axis and can include the angle perpendicular to the longitudinal axis. In this preferred embodiment, elements 30 rotate about their respective flexible hinges 31 in an outward direction away from the longitudinal axis-X. In the second position of tamp apparatus 10, elements 30 are preferably flexibly rotated to angle that is between greater than zero degrees and approximately 30 degrees from the first position.

In the second position of tamp apparatus 10, elements 30 have completed their deployment and the surfaces of terminal end 42 and terminal end 17 define a combined contiguous tamping surface of tamping apparatus 10. In this one preferred embodiment, in the second position terminal end 42 is approximately flush or even with terminal end 17 to form an annular tamping face that is approximately a plane perpendicular to the longitudinal axis. It is understood, however, that depending upon the desired application of tamp apparatus 10, the tamping surface defined by the combined terminal ends 42 and 17 can have a variety of shapes to include, for example, convex, faceted, angled from the perpendicular to the longitudinal axis or combinations thereof to further improve the application of tamping face 17. The term tamping surface as defined herein is a surface or surface area that can include one or more portions of cannula 12 and/or components, such as insert 9 and stylet 26, of tamp apparatus 10 that have an at least partially distally directed face and a structure suitable for use as a tamp.

The rotation of elements 30 between the first position and second position of tamp apparatus 10 can be assisted by stress relief devices such as, for example, notch 32, ribbing, and other means. In this preferred embodiment, the flexible hinge 31 for each element 30 is in proximity to the notch 32 for that element 30. The inner side of tubular wall. 22 can also include stress relief devices that assist the rotation and/or bias of elements 30. Notch 32 is preferably radially aligned and is positioned in proximity to the proximal terminal end of each element 30. Slots 28 can terminate in proximity to or extend proximal to notches 32.

The rotational movement of elements 30 from the first position to the second position is limited by a retention mechanism. The retention mechanism resists the rotation of flexible elements 30 from the first position to the second position by an external force, assists in the retaining of elements 30 in the deployed position and returns elements 30 to approximately the first position from the second or deployed position when the external force is removed. The retention mechanism can be produced by the material characteristics of the tubular wall 22 of elements 30 and/or, for example, a bias mechanism, such as a spring or an elastomer element that is integral to the hinge 31 of elements 30. In this preferred embodiment, the retention mechanism is a bias and/or resilience that is at least partially a result of the material characteristics of elements 30 of tubular wall 22.

In the second position of tamp apparatus 10, the proximal end portion 40 of stylet 26 and proximal end portion 18 of cannula 12 connect together to form a single integrated assembly. Proximal end portions 18 and 40 are structured to receive and/or transfer a force applied approximately along the aligned longitudinal axes-X and X' to the combined tamping surface of terminal ends 17 and 42.

Figure 12:
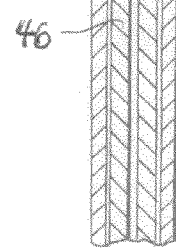
FIG. 12 is a side cross-sectional view of the distal end portions of the cannula and stylet of FIG. 11 taken along lines 12-12.

As shown in FIG. 12, in one preferred embodiment of stylet 26 tubular wall 46 of distal end portion 38 has a uniform diameter, rather than a taper. This change of the shape of distal end portion 38 can also result in a change of the tamping surface defined by terminal ends 17 and 42 of tamping apparatus 10 in the second position. Thus, the shape and size of tamping surface of tamp apparatus 10 can vary depending upon the intended application and includes factors such as the outside diameter of terminal end 17, diameter of opening 25, outside diameter of terminal end 42 and diameter of opening 52.

The changing of the shape of distal end portion 38 tubular wall 46 between a uniform, distally decreasing or distally increasing outside diameter selectively defines a desired combined tamping surface of terminal end 17 and terminal end 42 for a particular application. As one example, terminal end 42 can have a first diameter, spread elements 30 to a second diameter and define a first combined tamping surface of terminal ends 17 and 42. Similarly, terminal end 42 can have a second and larger diameter that spreads elements 30 to a third and larger diameter and a second combined tamping surface of terminal ends 17 and 42 that is larger than the first combined tamping surface. The tamping surface of the combined terminal ends 17 and 42 can also take a variety of shapes depending upon the desired application of tamp apparatus 10 as described previously for terminal 17 of cannula 12.

Figure 13:
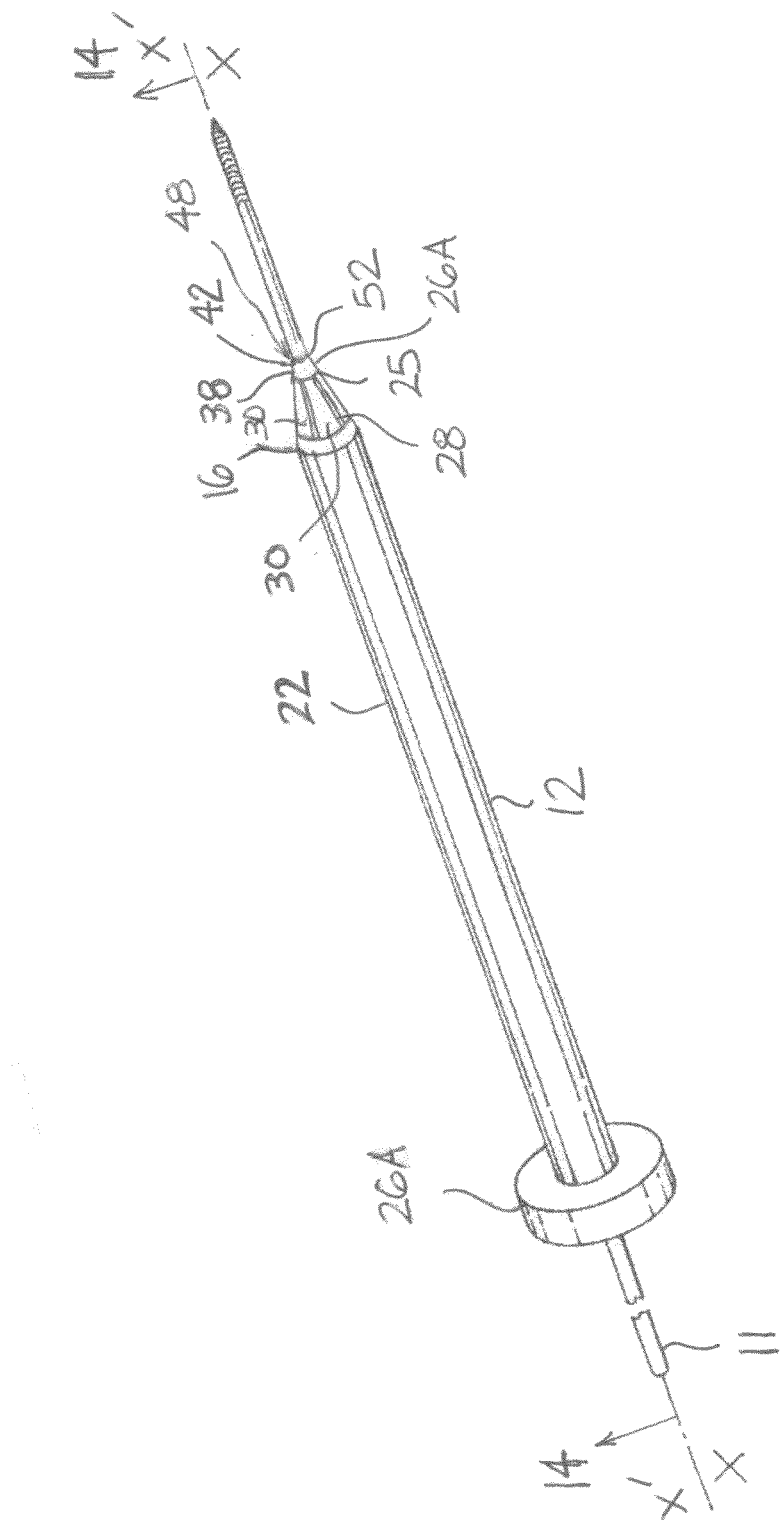
FIG. 13 is a side and front perspective view of a third embodiment of tamp apparatus of FIG. 2 in a first position that includes a plurality of hinged elements.
Figure 15:
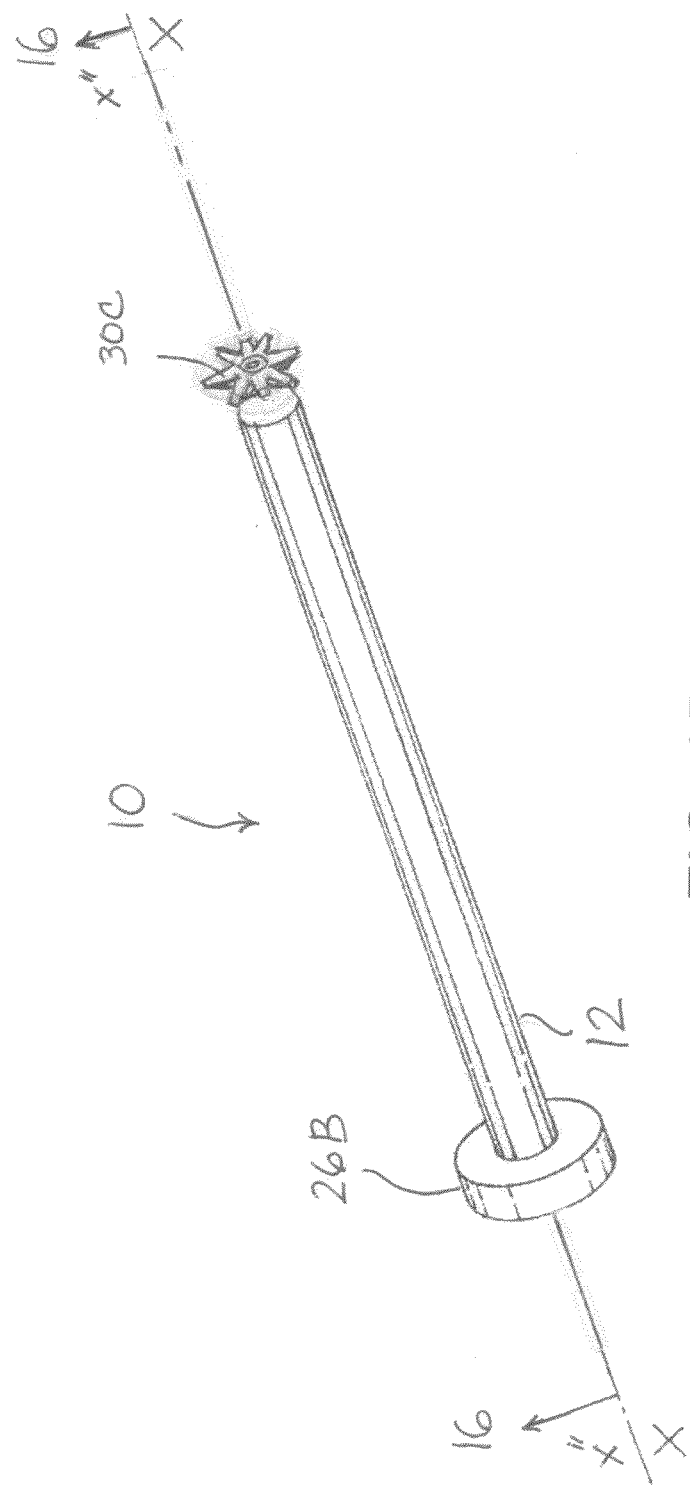
FIG. 15 is a side and front perspective view of a third embodiment of tamp apparatus of FIG. 2 in a second position that includes a plurality of hinged elements pivoted to define an increased tamping surface.

As shown in FIGS. 13 and 15, bone tamp apparatus 10 in a third preferred embodiment includes a cannula 12, a first stylet 26A and a second stylet 26B. Stylet 26A and 26B are separate components that can be selectively positioned into and removed from aperture 23 of cannula 12. Cannula 12 and stylet 26A are shown in a first position for penetration and/or passing through a body wall and into a portion of a body such as a joint and/or an anatomical cavity. Stylet 26A is a second cannula and defines a central longitudinal axis-X' that is aligned with longitudinal axis-X in the first position. Guide wire 11 can be selectively positioned in and removed from aperture 48 of stylet 26A.

In this preferred embodiment of tamp apparatus 10, distal end portion 16 of cannula 12 and distal end portion 38 of stylet 26A approximately form a truncated cone. Distal end portion 16 has an outside diameter that has a distally directed decreasing taper. Distal end portion 16 defines opening 25 of aperture 23. In this first position of tamp apparatus 10, distal end portion 38 of stylet 26A extends beyond opening 25 in the distal direction. Distal end portion 38 is also preferably a truncated cone with an outside diameter that has a distally directed decreasing taper. Terminal end 42 of stylet 26A defines second opening 52 of aperture 48.

Distal end portion 16 of cannula 12 includes a plurality of longitudinally aligned movable elements 30 that are separated by slots 28. Slots 28 can be in fluid communication with aperture 23 or include seals that preclude fluid communication from the environment external to tubular wall 22 to aperture 23 in the first position of tamp apparatus 10. The proximal terminal ends of slots 28 define the proximal terminal ends of elements 30.

In the first position, elements 30 extend in a distal direction. Elements 30 can be aligned with or at least partially offset from tubular wall 22. There are eight elements 30 in this one preferred embodiment, but it is understood that the number of elements can vary depending upon the intended application.

Figure 14:
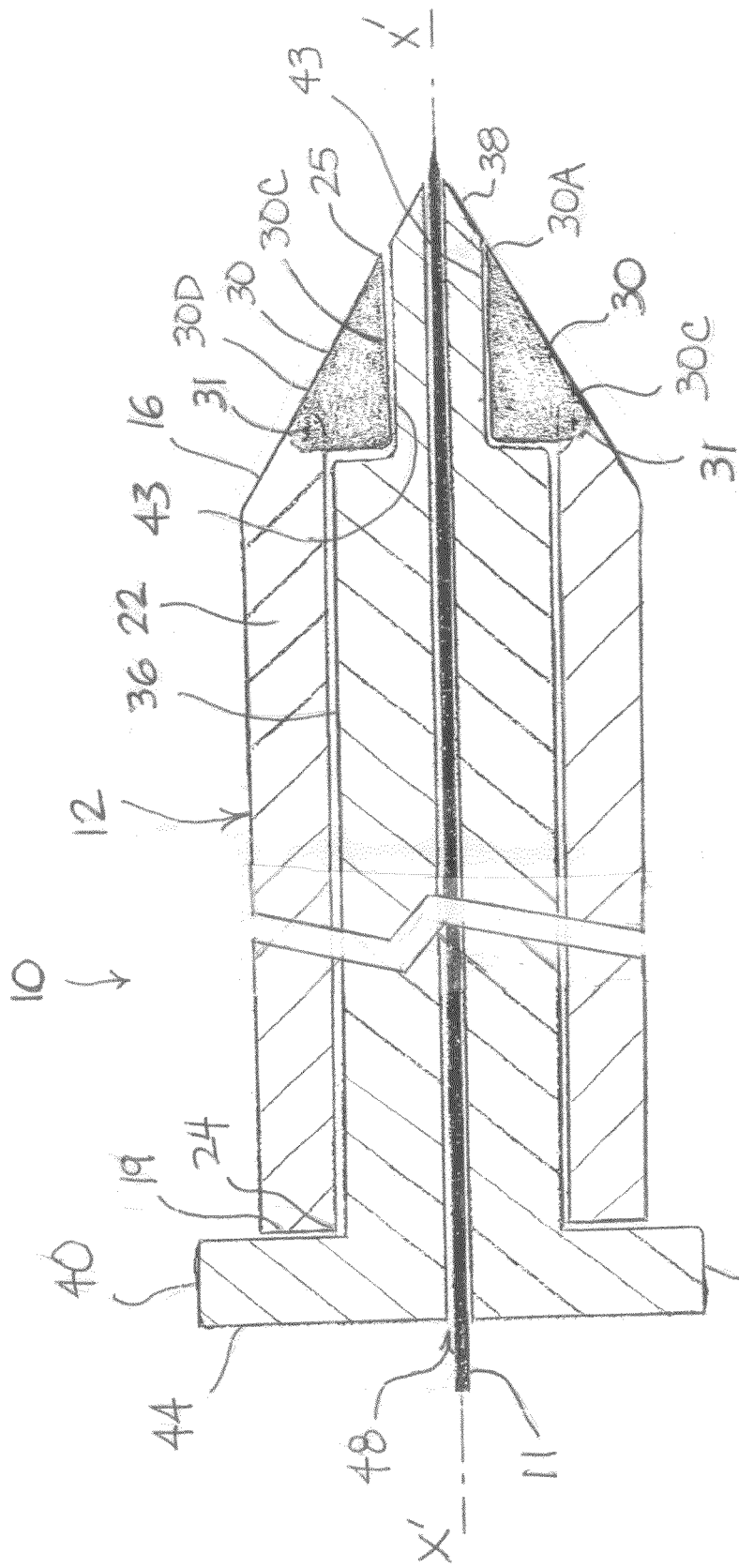
FIG. 14 is a cross-sectional view of the tamp apparatus of FIG. 13 along lines 14-14.

Referring now to FIGS. 13 and 14, two opposed elements 30 of the eight elements 30 in this preferred embodiment are shown. Elements 30 have an approximate wedge shape with a distally directed decreasing taper. Elements 30 have six walls including a distal end 30A, an opposed proximal end 30B, an inner surface or tamping face 30C, an outer surface 30D and two opposed sides 30E. Proximal ends 30B connect inner surfaces 30C and outer surfaces 30D. Proximal ends 30B and tamping faces 30C are preferably perpendicular. Tamping faces 30C are approximately aligned with the longitudinal axis-X and defines a portion of aperture 23 in the first position and. Outer surface 30D has taper that at least partially defines the tapered distal end portion 16 of cannula 12. Tamping face 30C has a distal edge and outer surface 30D has distal edge that are in proximity and connect to distal end 30A. Sides 30E preferably include a taper such that distal end 30A has a reduced width perpendicular to a radial axis from the longitudinal axis relative to the width of proximal end 30B.

Cannula 12 includes a plurality of pivotal connections 31 that couple each element 30 to tubular wall 22. In this preferred embodiment of tamp apparatus 10, connection 31 is a mechanical hinge and elements 30 rotate between the first position wherein elements 30 extend distally and are approximately aligned with the longitudinal axis-X and a second position. Connection 31 preferably connects the portions of elements 30 in proximity to the junction of proximal end 30B and outer surface 30D to tubular wall 22.

Stylet 26A includes center section 36 that is coupled to distal end portion 38 and proximal end portion 40. Distal end portion 38 includes a plurality of notches or cutouts 43. In this preferred embodiment, there are eight notches 43 and stylet 26A is aligned with cannula 12 such that each notch 43 receives at least a portion of an element 30. Aperture 48 has a diameter that receives the desired diameter of guide wire 11 for a given application of tamp apparatus 10.

Cannula 12 includes a retention mechanism that assists in the retaining of each element 30 in the first position. The retention mechanism can include, for example, a bias member such as a spring that urges elements 30 to the first position. Tubular wall 22 can also include, for example, a mechanical catch that retains elements 30 in the first position until a predetermined amount of force from an external source is exceeded. Similarly, a close fitting relationship between elements 30 and stylet 26A can, retain elements 30 in the first position and/or preclude any undesirable rotation of elements 30 about connections 31. Still further, each notch 43 can have a bias mechanism or shape that retains elements 30 in the first position such as a flexible distal lip.

Distal ends 30A of elements 30 define second opening 25 of aperture 23. In this preferred embodiment, second opening 25 has a diameter that is less than the diameter of first opening 24 in proximal terminal end 19. Aperture 23 is decreased by inner surfaces 30C of elements 30 that extend inside of the inner surface of tubular wall 22. The taper of outer surfaces 30D are approximately aligned with the taper of distal end portion 38 of first stylet 26A. It is understood that while distal end portion 16 of cannula 12 and distal end portion 38 of stylet 26A approximately have an approximately truncated cone shape, these two components can define alternative shapes in the first position depending upon the intended application such as for example, ogive, angular or planar.

Continuing with the third embodiment as shown in FIGS. 13 and 15, stylet 26A has been removed from aperture 23 and stylet 26B is positioned in aperture 23 of cannula 12. The second position of tamp apparatus 10 is defined by stylet 26B being fully positioned aperture 23 and connected to cannula 12 to form an integrated assembly. Stylet 26B defines a central longitudinal axis-X". Aperture 48 of stylet 26B is aligned with the longitudinal axis-X". Tamping faces 30C of elements 30 and terminal end 42 of stylet 26B define the tamping surface of tamp apparatus 10. Cannula 12, stylet 26A and stylet 26B are shown as straight and defining straight longitudinal axes-X, X' and X", but it is understood that cannula 12, stylet 26A and stylet 26B can have arcuate shapes.

Figure 16:
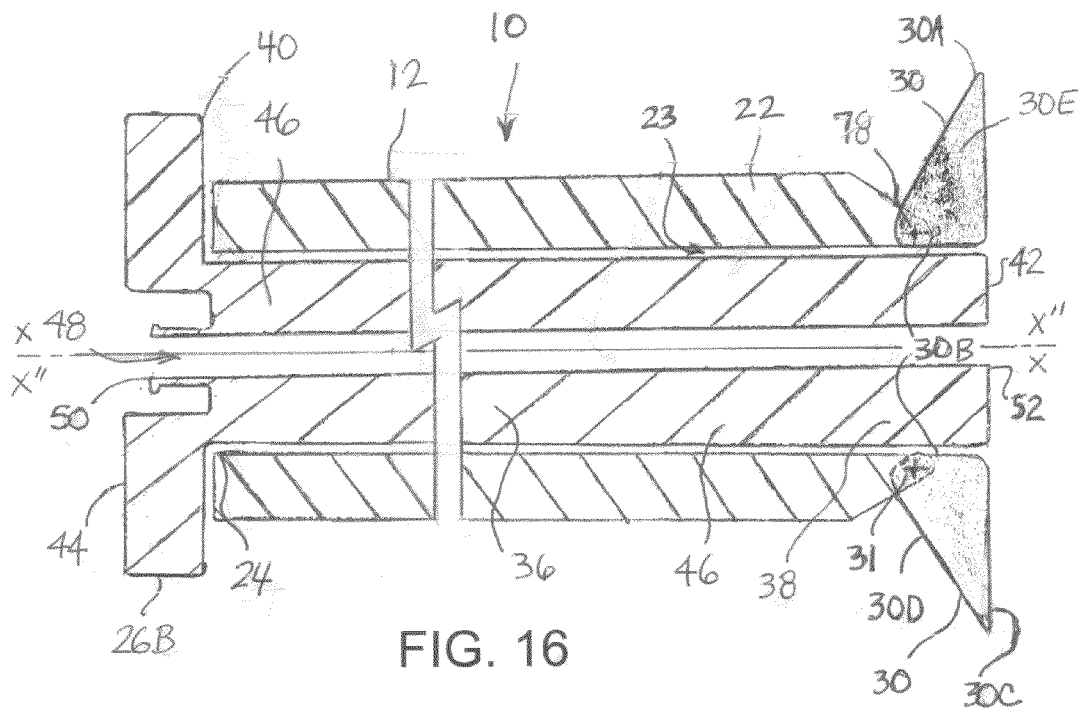
FIG. 16 is a cross-sectional view of the tamp apparatus of FIG. 15 along lines 16-16.

Referring now to FIGS. 15 and 16 stylet 26B is a third cannula that includes center section 36 that is coupled to distal end portion 38 and proximal end portion 40. Distal end portion 38 has a terminal end or tamping face 42 that is approximately perpendicular to the longitudinal axes X and X". Proximal end portion 40 includes proximal terminal end or base 44 that is suitable for driving tamp apparatus 10.

Stylet 26B tubular wall 46 defines aperture 48 that is in fluid communication with a first opening 50 defined in terminal end or base 44 and a second opening 52 defined in terminal end or face 42. Tubular wall 46 is a fluid tight conduit between openings 50 and 52 for the injection of bone graft. First opening 50 of stylet 26 can also define a standard interface such as leur lock, for example, for use with additional surgical instruments such as a syringe. Stylet 26B is approximately rigid along the longitudinal axis in that it directly transfers axially directed forces.

As stylet 26B is inserted into opening 24 of aperture 23 of cannula 12, distal end portion 38 of stylet 268 is placed into contact with elements 30. When tamp apparatus 10 is in the second position, distal end portion 38 has rotated elements 30 about connections 31 from the first position wherein elements 30 are approximately distally aligned to the second position wherein elements 30 are approximately perpendicular to the longitudinal axes X and X".

In this preferred embodiment, the portions of proximal ends 30B that extend below the inner surface of tubular wall 22 are directly contacted by tamping face 42 as stylet 26B moves distally. As stylet 26B continues distally, elements 30 rotate about connections 31 and deploy to the second position. In the first position of tamp apparatus 10 proximal ends 30B are approximately perpendicular to and tamping faces 30C are approximately aligned with the longitudinal axis. In the second position, elements 30 have rotated about hinges 31 approximately ninety degrees, proximal ends 30B are approximately aligned with the longitudinal axis and tamping faces 30C are approximately perpendicular to the longitudinal axes and directed distally. The distally directed movement of stylet 26B overcomes the force of the retention mechanism that biases elements 30 to the first position. The outer surface of tubular wall 46 of stylet 26B is in direct contact with and fixes the proximal ends 30B of element 30 in the second position. Distal end portion 16 of cannula 12 can also include a stop 78 that limits the rotational movement of elements 30 to the second position. Stop 78 is preferably connected to tubular wall 22 and can further assist in the retaining of elements 30 in the second position.

Figure 17:
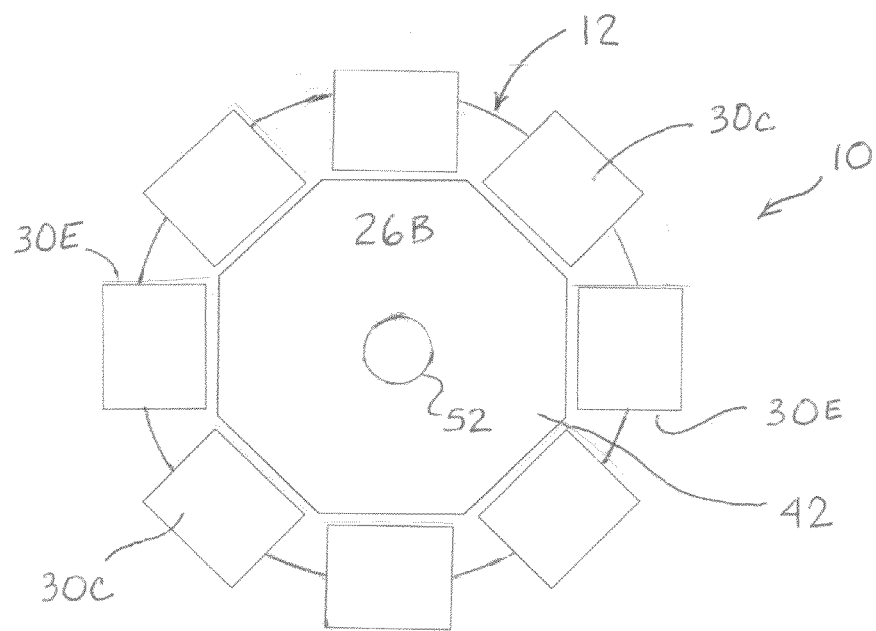
FIG. 17 is a front view of a distal end of the tamp apparatus of FIG. 15.

As shown in FIGS. 16 and 17, in the second position of tamp apparatus 10, terminal end 42 of stylet 26B and tamping faces 30C of elements 30 define the combined contiguous tamping surface of tamping apparatus 10. In this one preferred embodiment, in the second position terminal end 42 is approximately flush or even with inner surface 30C to form an annular tamping face that is approximately a plane perpendicular to the longitudinal axis. It is understood that depending upon the desired application of tamp apparatus 10, the tamping surface defined by the combined terminal end portion 42 and tamping face 30C can have a variety of two-dimensional and three-dimensional shapes to include, for example, convex, faceted, angled from the perpendicular to the longitudinal axis or combinations thereof.

Tamping faces 30C of the eight elements 30 in this preferred embodiment can also take a variety of shapes to facilitate particular applications of tamp apparatus 10 in the second position. The varying of the shapes includes the amount of taper, if any of sides 30E, the length of tamping face 30C in the radial direction from the longitudinal axis and width perpendicular to the radial direction of tamping face 30C. Opening 52 is the distal terminal end of aperture 23.

Figure 18:
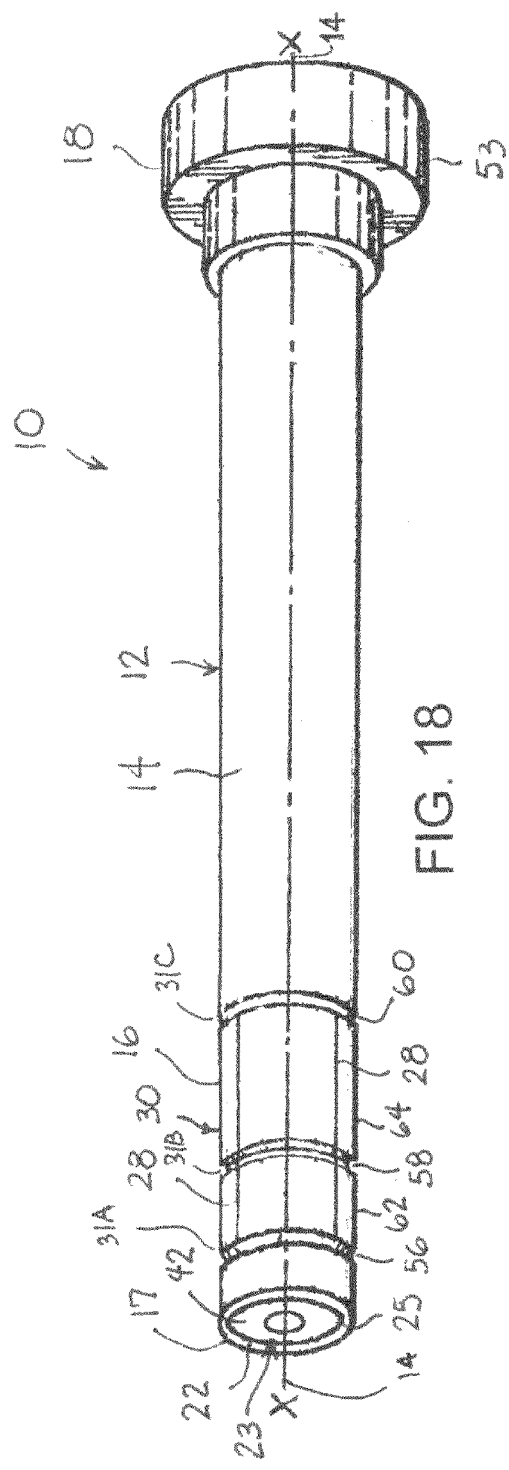
FIG. 18 is a side and front perspective view of a fourth embodiment of the tamp apparatus of FIG. 2 in a first position that includes multiple hinges for the movement of the elements constructed in accordance with the present disclosure.

As shown in FIG. 18 in a fourth preferred embodiment of tamp apparatus 10, cannula 12 includes central section 14, distal end portion 16, and proximal end portion 18 that define central longitudinal axis-X. Stylet 26 in this embodiment is concentrically mounted and slidably secured within aperture 23 of tubular portion 14 in an adjoined close fitting relationship. Terminal end 17 has an annular shape that defines opening 25 of aperture 23. Terminal end 17 is fixed relative to tubular wall 22 and stylet tamping face 42. Cannula 12 and stylet 26 are shown as being straight, but can also have an arcuate shape. Tamp apparatus 10 is shown in the first position.

In this preferred embodiment, cannula 12 defines a plurality of longitudinally aligned slots 28 that separate a plurality of elements 30. Slots 28 can be in fluid communication with aperture 23 or include seals that preclude fluid communication from the environment external to tubular wall 22 to aperture 23 in the first position of tamp apparatus 10. The proximal and distal terminal ends of slots 28 approximately define the proximal and distal terminal ends of elements 30. Each element 30 includes a plurality of hinges 31. Tubular wall 22 preferably includes devices for stress relief that are positioned in proximity to each of the hinges 31 of elements 30.

In this one preferred embodiment of tamp apparatus 10 distal end portion 16 has four longitudinally aligned slots 28 that separate tubular wall 22 into four elements 30. Each element 30 has three hinges 31. A first or distal hinge 31A is in proximity to a first notch 56, a second hinge 31B is in proximity to a second notch 58 and a third hinge 31C is in proximity to a third notch 60. A distal first member 62 of each element 30 extends between the first notch 56 and the second notch 58. A proximal second member 64 of each element 30 extends between second notch 58 and third notch 60. In this preferred embodiment, the hinges 31A, 31B and 31C of elements 30 are flexible hinges in tubular wall 22 that are in proximity to each of notches 56, 58 and 60. Notches 56, 58 and 60 provide stress relief, as described previously, that aid elements 30 in rotating about their respective hinges 31A-C.

Figure 19:
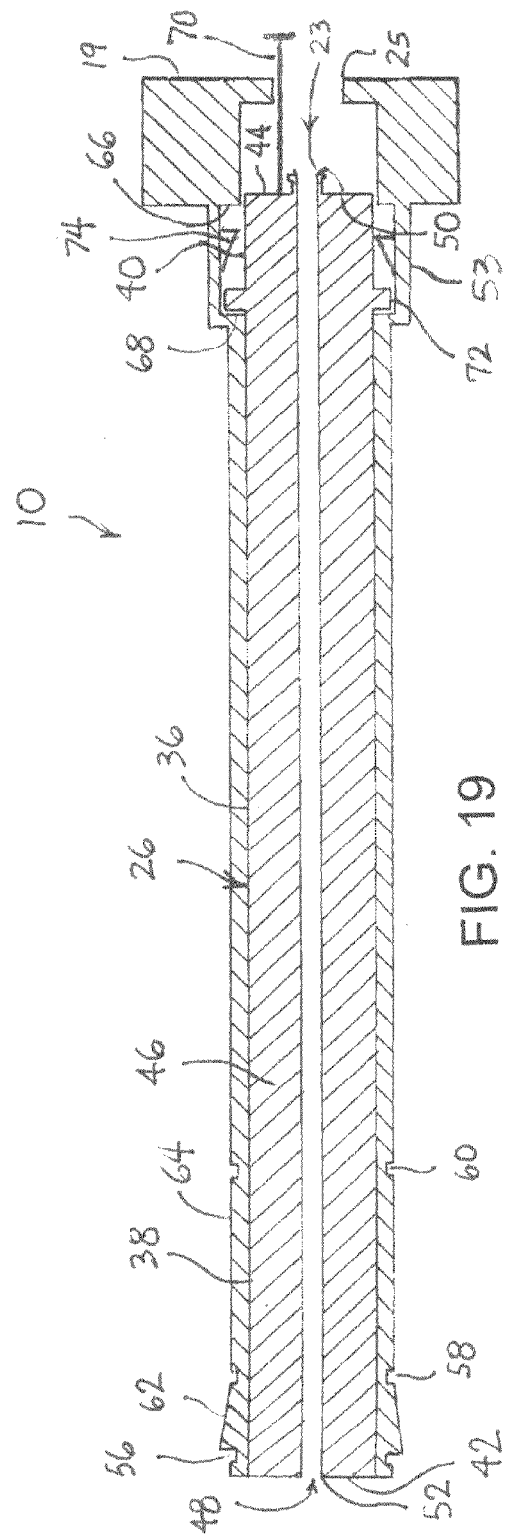
FIG. 19 is a cross-sectional view of the tamp apparatus of FIG. 18 along lines 19-19.
Figure 22:
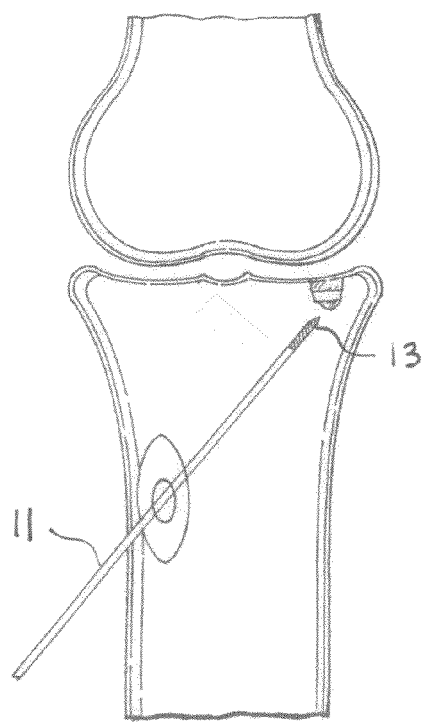
FIG. 22 is a simplified side view of a distal end of the guide wire of FIG. 2 being inserted through a surgical incision and being positioned in proximity to the tibial plateau fracture.
Figure 23:
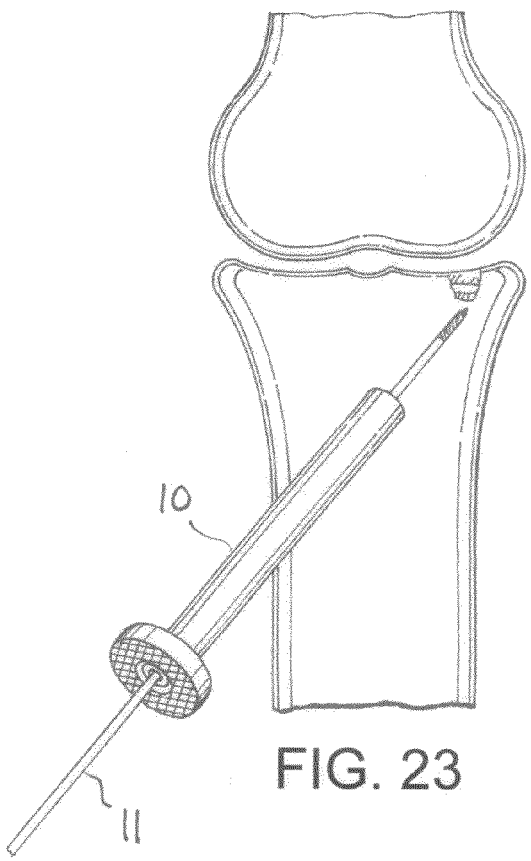
FIG. 23 is a simplified side view of the tamp apparatus of FIG. 2 being inserted through the surgical incision and being guided towards the tibial plateau fracture by the guide wire.

In this preferred embodiment, the hinges 31 are preferably flexible hinges and tubular wall 22 has material characteristics that accommodate the rotational movement of elements 30 between the first position and the second position of tamp apparatus 10. The hinge 31 can also be a mechanical joint and/or have the configuration of a pivot, for example. As shown in FIGS. 18 and 19, stylet 26 includes central section 36, distal end portion 38 and proximal end portion 40 that are aligned with central longitudinal axis-X. Stylet 26 has a tubular wall 46 that is a fluid tight conduit that defines an aperture 48. Aperture 48 extends between opening 50 defined in proximal end portion 40 and opening 52 defined in terminal end or tamping face 42. Aperture 48 is preferably aligned with the longitudinal axis-X.

The distal end portions 16 and 38 of cannula 12 and stylet 26 are-connected together in proximity to terminal ends 17 and 42. The connection of terminal ends 17 and 42 is preferably by a snap-fit detent, such that cannula 12 and stylet 26 can be readily assembled and disassembled. It is understood, however, that the connection of terminal ends 17 and 42 can be by any conventional technique to include a spot weld, a heat bond, an adhesive and/or any type of mechanical connection such as threaded interface.

Proximal end portion 18 in this preferred embodiment includes a housing 53 that defines a proximal stop 66 and a distal stop 68. Proximal end portion 40 of stylet 26 extends into housing 53. Base 44 of stylet 26 is set apart a predetermined distance within housing 53 from base 19 of cannula 12 in the first position of tamp apparatus 10.

Base 19 of proximal end portion 18 is a wall that defines the proximal opening 25 to the interior of housing 53 and aperture 23. Opening 25 provides access to base 44 and opening 50 of stylet 26. Opening 50 can include a standard interface such as a leur lock, for example, for use with a syringe or additional surgical instruments. Base 44 can also include a handle 70 that extends proximal to housing 53. The leur lock and/or handle 70 can be used to grasp base 44 and pull stylet 26 proximally relative to cannula 12 thereby deploying flexible elements 30.

Proximal end portion 40 of stylet 26 includes a protuberance or ridge 72 that extends radially outward from tubular wall 46 in proximity to base 44. Ridge 72 is preferably a radially aligned annular wall. Ridge 72 abuts distal stop 68 in the first position of tamp apparatus 10. Tamp apparatus 10 also includes a lock 74 that fixes the relative positions of cannula 12 and stylet 26 in the second position.

Referring now to FIGS. 19-21, tamp apparatus 10 moves from the first, position to the second position by the distal displacement of cannula 12 along the longitudinal axis-X relative to stylet 26. In this preferred embodiment, the movement of tamp apparatus 10 from the first position to the second position includes the deploying and rotating of first members 62 and second members 64 of elements 30 about their respective hinges 31A, 31B and 31C. Proximal end portion 40 of stylet 26 is displaced proximally relative to housing 53 of cannula 12. In the second position, the outer surfaces of first members 62 define a distally directed tamping face that is an additional portion of the tamping surface of tamping apparatus 10.

In the second position, the tamping face of first members 62 is combined with the tamping surfaces of terminal end 42 of stylet 26 and terminal end 17 of cannula 12 to define the combined tamping surface of tamp apparatus 10. Tamp apparatus 10 can be constructed such that first members 62 can deploy from an angle greater than zero degrees to an oblique angle that is at least slightly greater than ninety degrees to form an approximately concave tamping surface. Elements 30 are fabricated of materials and have tubular wall thicknesses that define a structure in the second position that can function as a bone tamp. The angled positions of second members 64 provide structural support for the oblique angles of first members 62.

In the second position of tamp apparatus 10, proximal end portion 40 is displaced proximally relative to and within housing 53. The relative proximal displacement of proximal end portion 40 in this preferred embodiment is halted by ridge 72 abutting proximal stop 66 of proximal end portion 18. In this preferred embodiment, housing 53 includes lock 74 that secures ridge 72 abutting proximal stop 66. Lock 74 prevents the distal movement of stylet 26 relative to cannula 12 in the second position that could undesirably return tamp apparatus 10 to the first position. Proximal end portion 18 preferably includes a release mechanism such as a switch that deactivates lock 74 and allows the return of stylet 26 to the first position of tamp apparatus 10.

In this embodiment, lock 74 can further include fixing the relative positions of cannula 12 and stylet 26 in multiple intermediate positions between the first position and second position of tamp apparatus 10. Lock 74 can include elements well known in the art such as multiple engaging teeth or protuberances and insets, for example that can be engaged, locked and released from each position. These intermediate positions can selectively vary the angular deployment of elements 30 and thereby alter the shape of the tamping surface during operational use.

As shown in FIGS. 2-3 and 22-23, the first embodiment of tamp apparatus 10 in operation shows the distal end 13 of guide wire 11 being introduced through a pre-existing incision in a leg and positioned at a point directly beneath a depressed fragment of bone or fracture of the tibial plateau. Tamp apparatus 10 is slid over the pre-positioned guide wire 11, through the incision and is positioned directly beneath the depressed fragment of bone. Guide wire 11 can be further used to align tamp apparatus 10 relative to the fracture.

Figures 24, 25:
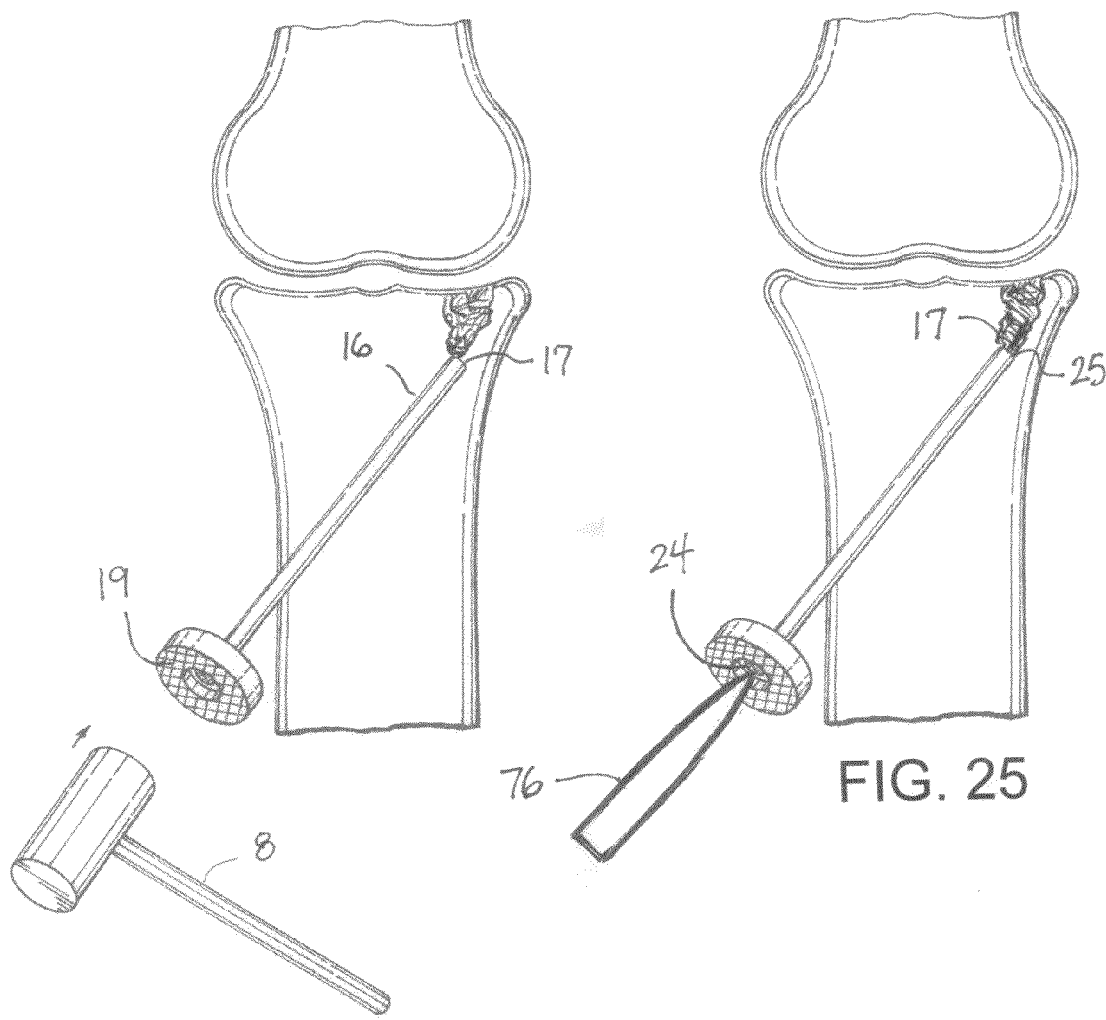
FIG. 24 is a simplified side view of the tamp apparatus of FIG. 2 being aligned for displacing a tibial plateau fracture.
FIG. 25 is a simplified side view of the tamp apparatus of FIG. 2 injecting bone graft into the void created by the bone tamp as the bone tamp is withdrawn from the tibia.
Figure 26:
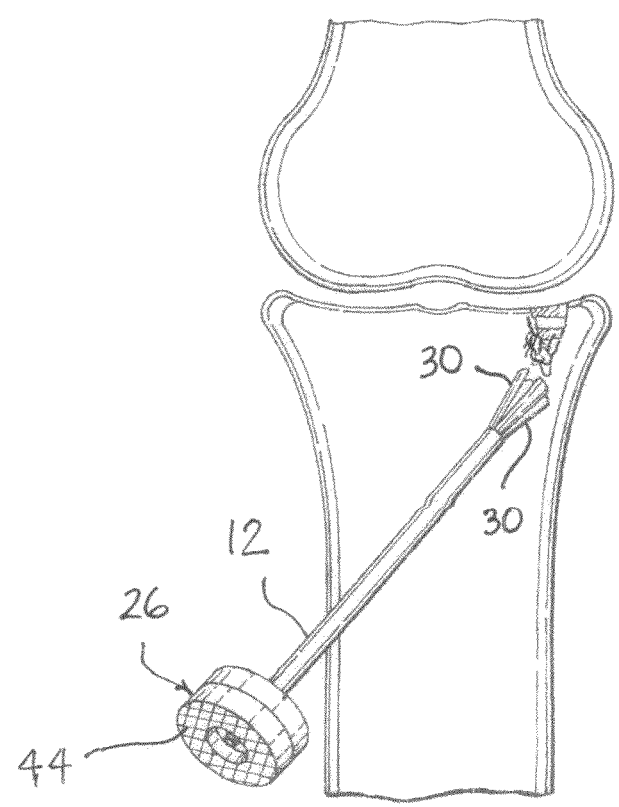
FIG. 26 is a simplified side view of the tamp apparatus of FIG. 4 in a second position positioned in a tibia, the cannula and stylet connected and the elements deployed to define an increased tamping surface.
Figure 27:
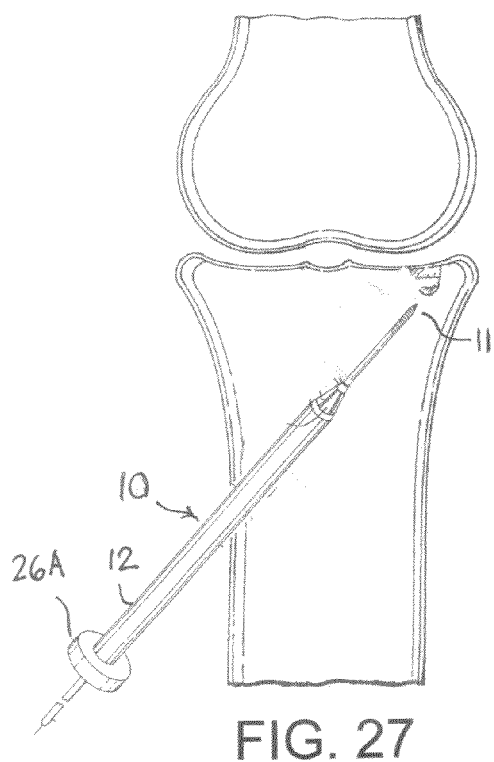
FIG. 27 is a simplified side view of the tamp apparatus of FIG. 13 in a first position that includes the cannula and a first stylet being inserted into a tibia.
Figure 28:
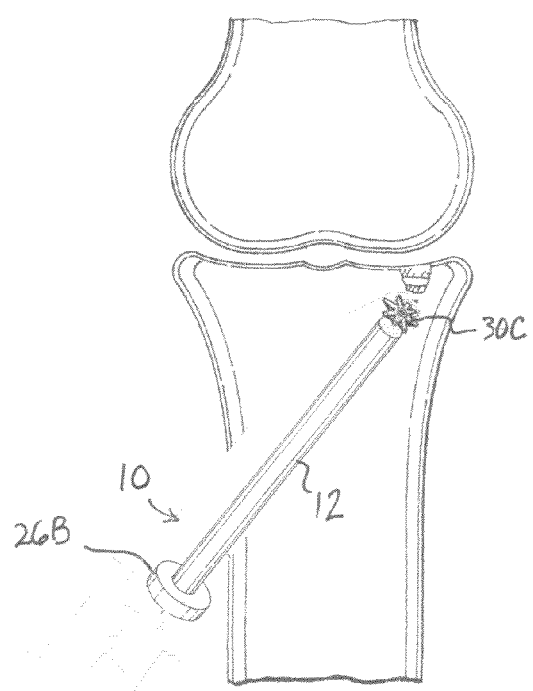
FIG. 28 is a simplified side view of the tamp apparatus of FIG. 13 in a second position that includes the cannula and a second stylet positioned in the tibia, the elements deployed to define an increased tamping surface.
Figure 29:
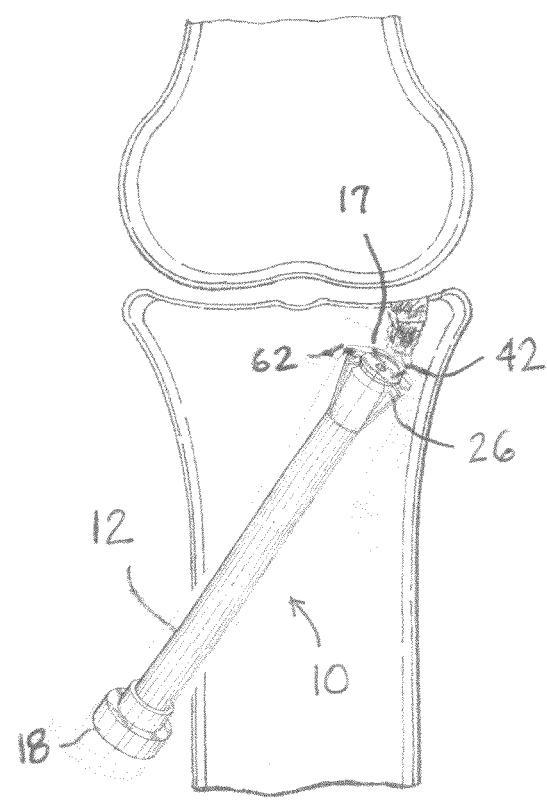
FIG. 29 is a simplified side view of the tamp apparatus of FIG. 18 in second position in a tibia with the elements deployed to define an increased tamping surface.

Referring now to FIGS. 2-3 and 24, guide wire 11 is then withdrawn leaving tamp apparatus 10 in position for treating the fracture. Tamping face 17 of distal end portion 16 is in direct contact with the bone that is to be displaced, central section 16 extends through the incision and proximal end portion 18 is clear of the patient. Mallet 8 is preferably used to strike base 19 and drive tamping face 17, the tamping surface, into the tibia to displace and the return the depressed portion of the bone to a natural position. Insert 9 can be selectively employed to with cannula 12 to augment the tamping surface of tamp apparatus 10. The operational employment of insert 9 in aperture 23 can be especially advantageous to any of the embodiments herein when a larger diameter aperture 23 (or aperture 48, see FIG. 7) is required. A larger diameter aperture 23 can be required, for example, when bone chips are added to or included in the bone graft or a more viscous bone graft is employed. The increased size of aperture 23 can result in a narrowing of tamping face 17 of cannula 12 that can be compensated by the selective employment of insert 9.

As shown in FIG. 25, once the displacing of the fracture is completed insert 9 is removed as required and a source of bone graft 76 is connected to first opening 24 of cannula 12. The bone graft is supplied under pressure through aperture 23 to second opening 25. First opening 24 defines an interface that is suitable for connecting with the external source of bone graft 76.

As the bone graft is injected from second opening 25 into the bone void, cannula 12 can be gradually withdrawn. The filling of the void by the bone graft and the withdrawal of the cannula can then be repeated until the bone void is completely filled with bone graft. This process advantageously prevents the accumulation of blood and fatty bone marrow in the bone void which can occur when the tamp is removed prior to the placement of the bone grail When blood and fatty bone marrow is allowed to fill the bone void during this procedure, the integration of the bone graft with the native bone can be compromised.

After the bone void is tilled, terminal end 17 can be used to tamp the graft in position. This can be done sequentially after each injection and gradual withdrawal as well as after the bone graft injecting is completed. Alternatively, cannula 12 can inject bone graft continuously into the bone void as tamp apparatus 10 is withdrawn. Insert 9 can be employed as desired once bone graft injection is completed. The tamping of the bone graft can help to ensure that any voids left during the injection are filled and the bone graft is condensed within the tibia. When the injection and tamping of the bone graft is completed, cannula 12 is withdrawn, from the incision.

Tamp apparatus 10 in this and any of the embodiments can have an arcuate or straight shape depending upon the desired application. The arcuate shape has the advantage that the directional thrust of terminal end 17 can be oriented to displace the depressed bone fragment at an angle that has a closer alignment to the direction of the fracture in the tibial plateau. The straight tamp apparatus 10 can compensate for this by having a tamping face that has a specialized shape.

Referring now to FIGS. 4-12 and 22-26, the second embodiment of tamp apparatus 10 in operation is initially the same as that for the first embodiment. The distal end of guide wire 11 is introduced through an incision in a leg to a point directly beneath a depressed fragment of bone or fracture of the tibial plateau. Cannula 12 is initially slid over the pre-positioned guide wire 11, through the incision and is positioned directly beneath the depressed fragment of bone. Stylet 26 is slid over guide wire 11 and central section 36 and distal end portion 38 are inserted through second opening 25 and into aperture 23. Guide wire 11 can be timber used to align tamp apparatus 10 relative to the fracture.

Once tamp apparatus 10 is aligned with the fracture, tamping face 42 of stylet 26 is moved through the distal end of aperture 23 and elements 30 are displaced our deployed from the first position to the second position of tamp apparatus 10. In the second position elements 30 have been rotated about flexible hinges 31 and are deployed to a predetermined angle oblique to the longitudinal axis-X. The tamping surface of tamp apparatus 10 in this second embodiment combines the approximately aligned surfaces of terminal end 42 and terminal end 17. The proximal end portion 40 of stylet 26 and proximal end portion 18 of cannula 12 are connected together as a single assembly. Guide wire 11 is removed from the procedure through aperture 48.

With tamp apparatus 10 in the second position and aligned with the fracture, mallet 8 is preferably used to strike or tap base 44 and/or proximal end portion 40 of stylet 26. The combined tamping surface of terminal ends 17 and 42 is driven into the tibia to displace and return the depressed portion of the bone to a natural position. The expanded tamping surface tamp apparatus 10 in the second embodiment advantageously decreases the stress placed on the fracture fragments during tamping and allows for minimal bone window and incision size. It is understood that tamp apparatus 10 can include one or more stylet 26 and that multiple stylet 26 can be selectively employed during a single surgical procedure to change the amount or the shape of the combined tamping surface.

Once the displacing of the fracture is completed, a source of bone graft 76 is connected to first opening 50 of stylet 26 and is supplied under pressure through aperture 46 to second opening 52. The pressure from source of bone graft 76 is sufficient to displace any bone material that has penetrated into aperture 23 during tamping. The bone graft is injected from opening 52 into the bone void as tamp apparatus 10 is withdrawn. The filling of the void by the bone graft and the withdrawal of tamp apparatus 10 can then be repeated until the bone void is completely filled with bone graft. Alternatively, stylet 26 can inject bone graft continuously into the bone void as tamp apparatus 10 is gradually withdrawn.

After the injecting of the bone graft is completed, the combined tamping surface of terminal ends 17 and 42 can be used to tamp the bone graft in position as described above. When the tamping is completed, stylet 26 is withdrawn from aperture 23 and the elements 30 of cannula 12 return to approximately the first position by the retention mechanism of cannula 12 and/or the interface with stylet 26. With elements 30 in the first position, cannula 12 is withdrawn from the incision.

Referring now to FIGS. 13-17, 27 and 28, the third embodiment of tamp apparatus 10 in operation includes the introduction of the distal end of guide wire 11 as described previously. Cannula 12 and stylet 26A in the first position are slid over the pre-positioned guide wire 11 and used to approach the depressed fragment of bone. Stylet 26A is then withdrawn from the patient.

Stylet 26B is slid over the pre-positioned guide wire 11 and inserted through opening 24 of aperture 23 of cannula 12 and distal end portion 38 of stylet 26B deploys elements 30 about connections 31 from the first position wherein elements 30 are approximately distally aligned to the second position wherein elements 30 are preferably perpendicular to the longitudinal axis.

In this preferred embodiment, the portions of proximal ends 30.B that extend below the inner surface of tubular wall 22 are contacted by face 42 of stylet 26B and rotated about connections or hinges 31 as face 42 moves distally displacing proximal end 30B to a position that is approximately aligned with the longitudinal axis. Inner surface or tamping face 30C is then directed distally and fixed in position to define the second position of tamp apparatus 10. The tamping surface of tamp apparatus 10 in the second position includes the distally directed tamping faces 30C and stylet 26B distal terminal end 42. As a result of the right angle relationship between proximal end 30B and tamping face 30C in this preferred embodiment, the deployment of elements 30 to the second position of tamp apparatus 10 by stylet 26B rotates elements 30 approximately 90 degrees.

In the second position of tamp apparatus 10, the proximal end portion 40 of stylet 26B and proximal end portion 18 of cannula 12 preferably connect together to form a single integrated assembly. Proximal end portions 18 and 40 are structured to receive and/or transfer a force applied approximately along the aligned longitudinal axes-X and X' to the combined tamping surface of tamp apparatus 10.

Once tamp apparatus 10 is aligned with the fracture, guide wire 11 is withdrawn from cannula 12 and stylet 26B. The integrated cannula 12 and stylet 26B are held in position and mallet 8 is used to strike or tap base 44 (See FIG. 24). The combined tamping surface of terminal end 42 and tamping faces 30C is driven into the tibia to displace and correct the fracture to a natural position. Once the tamping of the fracture of the tibial plateau is completed, bone graft is injected into the bone void as described previously through aperture 48 of stylet 26B. The bone graft fills the bone void and tamping apparatus 10 is returned to the first position by withdrawing stylet 26B from cannula 12. As required, first stylet 26A can be reinserted into aperture 23 of cannula 12.

As shown in FIGS. 18-25 and 29, the fourth embodiment of tamp apparatus 10 in operation includes the introduction of the distal end of guide wire 11 as described previously. Cannula 12 and stylet 26 are an integrated assembly that is slid over the pre-positioned guide wire 11 and positioned directly beneath the depressed fragment of bone. Stylet 26 is moved in aperture 23 relative to cannula 12 to reposition elements 30 from the first position to the second position of tamp apparatus 10. One process for doing this includes holding onto proximal end portion 18 of cannula 12 and displacing stylet 26 proximally in aperture 23 using an instrument attached to the leur lock of aperture 50 of base 44 and/or handle 70.

As cannula 12 advances distally relative to stylet 26 along the longitudinal axis-X, the connection at terminal ends 42 and 1,7 force the hinges 31 of elements 30 to rotate. As cannula 12 moves relative to stylet 26, lock 74 of cannula 12 is displaced by ridge 72 of stylet 26. Once ridge 72 has passed lock 74 and tamp apparatus 10 is in the second position, lock 74 returns to the extended or locked position and secures cannula 12 in position relative to Stylet 26 in the second position of tamp apparatus 10. Ridge 72 is fixed in position between lock 74 and proximal stop 66 in housing 53. This position locks the angular relationship or second member 64 and first member 62 of cannula 12 in a fixed position with sufficient rigidity and structural integrity to perform bone-tamping procedures. Guide wire 11 is removed from the procedure through aperture 48.

Once tamp apparatus 10 is aligned with the fracture, cannula 12 is preferably held by proximal end portion 18 and mallet 8 is used to strike or tap base 19. The combined tamping surface of terminal ends 17 and 42 with distal first members 62 of elements 30 is driven into the tibia to displace and return the depressed portion of the bone to a natural position. Once the tamping of the fracture of the tibial plateau is completed, bone graft is injected into the bone void as described previously. The bone graft fills the bone void and tamping apparatus 10 is returned to the first position by releasing lock 74 and forcing stylet 26 distally relative to cannula 12. Tamp apparatus 10 is then withdrawn from the incision.

The expanded tamping surface of tamp apparatus 10 in the embodiments herein advantageously decrease the stress placed on the fracture fragments during tamping and allow for minimal bone window and incision size. Aperture 23 and aperture 48 provide a passageway for guide wire 11 that enables tamp apparatus 10 to be guided directly into the desired position and angle for tamping. In addition, aperture 48 provides the advantage of a conduit that can supply, inject and tamp the injected bone graft continuously into the bone void as tamp apparatus 10 is withdrawn from the bone void.

Cannula 12 and stylet 26 (to include stylet 26A and 26B) can be made of materials suitable for medical applications such as but not limited to polymers, composites and metals. Tamp apparatus 10 is preferably a reusable assembly that can be disassembled as required and sterilized, but it can also be constructed as a disposable device. Cannula 12, stylet 26 and insert 9 are approximately incompressible along their respective longitudinal axes for their intended applications.

In the preceding specification, the present disclosure has been described with reference to specific exemplary embodiments thereof. It will be evident, however, that various modifications, combinations and changes may be made thereto without departing from the broader spirit and scope of the invention as set forth in the claims that follow. For example, while the tamp apparatus 10 is described herein as adapted for use with insert 9 and guide wire 11, it is understood that the tamp apparatus 10 can be selectively used without insert 9 and guide wire 11. In addition, though the present invention is described in terms of a series of embodiments, each embodiment of the present invention can combine one or more novel features of the other embodiments. The specification and drawings are accordingly to be regarded in an illustrative manner rather than a restrictive sense.

What is claimed is:

1. A tamp apparatus for use in surgical operations for the realignment of fractured bone, the tamp apparatus comprises:
    a cannula that has a tubular wall that includes a distal end portion and a proximal end portion, the distal end portion includes a distal terminal end and the proximal end portion includes a proximal terminal end;
    a lumen defined by the tubular wall of the cannula, the lumen extends from a first opening defined in the proximal terminal end to a second opening defined in the distal terminal end, the first opening optionally adapted to couple with a source of bone graft material and the second opening optionally adapted for the injecting of bone graft material;
    a distally directed tamping face of the cannula adapted for the displacement of bone from a fractured position to an approximately natural position, the tamping face defined by the distal terminal end of the distal end portion of the cannula between an outside diameter of the tubular wall of distal terminal end and an outside diameter of the second opening;
    a central longitudinal axis defined between the distal end portion and the proximal end portion of the cannula, the distal end portion includes a plurality of slots defined in the tubular wall and the slots define a plurality of elements, each element includes a distally directed taper of the inner surface of the cannula tubular wall that decreases the diameter of the cannula second opening, the elements movable between a first position wherein the elements are approximately aligned with the longitudinal axis and a second position wherein the elements are oblique to the longitudinal axis, the slots extend from the distal terminal end proximally to a terminal end of the slot, the tamping face of the cannula includes a distal end of each element, the tubular wall includes a hinge in proximity to the terminal end of the slot for the movement of each element between the first position and the second position, the elements in the second position rotatably moved outward from the central longitudinal axis about the hinge, the elements including a retention mechanism, the retention mechanism resists the rotation of the elements from the first position to the second position and biases the elements to the first position; and
    a stylet that includes a distal end portion and a proximal end portion, the stylet distal end portion includes a distally directed end that defines a stylet tamping face, the stylet approximately axially rigid, the stylet movable in the lumen of the cannula to contact the distally directed tapered inner surface of the cannula tubular wall and move the elements from the first position to the second position, the cannula and stylet of the tamp apparatus fixed in the second position, a tamping face of the tamp apparatus in the second position defined by the distal ends of the elements of the cannula and distal end of the stylet.

2. The tamp apparatus of claim 1, wherein in the first position the cannula first opening has a first diameter and the cannula second opening has a second diameter, in the first position the diameter of the cannula first opening is larger than the diameter of the cannula second opening, the cannula tubular wall includes a tapered inner surface that decreases to the diameter of the second opening and increases the surface of the cannula tamping face.

3. The tamp apparatus of claim 1, wherein the stylet defines an aperture that extends between a proximal opening in the proximal end portion and a distal opening in the distal end portion of the stylet, the proximal opening of the aperture of the stylet is adapted to connect to an external source of bone graft material and the stylet is, adapted to inject the bone graft material under pressure from the distal opening of the aperture.

4. The tamp apparatus of claim 1, wherein the stylet provides a displacing force to the distally directed taper of the elements, to move the elements between the first position and the second position, the tamping face of the tamp apparatus includes the distal end of the stylet and distal ends of the elements in the second position fixed in approximate alignment.

5. The tamp apparatus of claim 1, wherein the elements are returned from the second position to approximately the first position by the retention mechanism and withdrawal of the stylet interface with the distally directed taper of the elements.

6. The tamp apparatus of claim 1 that further includes a guide wire.

7. The tamp apparatus of claim 1, wherein the proximal end portions of the stylet and cannula connect together and are structured to receive and transfer force along the longitudinal axis to the combined tamping face of the terminal ends of the cannula and stylet.

8. The tamp apparatus of claim 1, wherein the stylet includes at least two cylindrical shaped stylets with different distal end shapes, the stylets selectable to define a desired shape of a surface of the tamping face in the second position.

9. The tamp apparatus of claim 1, wherein the tamp apparatus includes a proximal end portion and the proximal end portion includes a base, the cannula and stylet fixed in the second position and the base adapted to receive an external force and transfer the external force from the base to the tamping face of tamp apparatus.

10. The tamp apparatus of claim 1, wherein the stylet includes at least two stylets with distal end portions that include tubular walls of differing diameters and the diameter of the distal end portion of each stylet is selected to define a desired combined diameter of tamping face of the stylet and cannula in the second position.

11. The tamp apparatus of claim 1, wherein the tamp apparatus in the second position is adapted to displace at least cancellous bone.

12. A method of treating a bone fracture using a tamp apparatus comprising the steps of:
 introducing a guide wire through a hole cut in a cortex of a bone and positioning a distal end of the guide wire in proximity to a bone fracture;
 coupling a longitudinally aligned lumen of a cannula of the tamp apparatus to the guide wire and positioning a distally directed tamping face of the cannula of the tamp apparatus for treating the bone fracture, the tamp apparatus further including a stylet with a distal end tamping face;
 inserting the stylet into the lumen and connecting the stylet and cannula of the tamp apparatus into an integrated tamp apparatus assembly, the tamp apparatus includes a distal end of the cannula defining a plurality of movable elements that are longitudinally aligned in a first position with a central longitudinal axis defined by the cannula and the plurality of elements biased to the first position, the inserting of the stylet in the lumen deploying the elements outward from the first position of longitudinal alignment to a second position oblique to the longitudinal axis, the second position includes the approximate alignment of the distal end of the stylet and distal ends of the elements, the second position fixing the positions of the stylet and cannula, the combined stylet and cannula tamp apparatus in the second position increasing the area of a tamping face of the tamp apparatus;
 treating the bone fracture by striking a proximal end of the tamp apparatus and using the tamping face of the tamp apparatus to displace and return the fractured bone to an approximately natural position.

13. The method of treating a bone fracture of claim 12 further comprising the step of removing the guide wire from the tamp apparatus when the tamp apparatus is positioned for treating the fracture.

14. The method of treating a bone fracture of claim 12 further comprising the step of selectively positioning the elements of the tamp apparatus from the first position with a first tamping face surface area and first diameter of the cannula and the second position with a second tamping face surface area that includes the combined distal ends of the cannula and stylet, the second tamping face surface area and diameter being greater than the first tamping face surface area and diameter.

15. The method of treating a bone fracture of claim 12, wherein the stylet defines an aperture that extends between, a distal opening in a distal terminal end and a proximal opening in a proximal, terminal end of the stylet and further comprising the step of injecting bone graft material through the distal opening of the lumen of the tamp apparatus, the bone graft material filling the voids left by the corrective repositioning of the fractured bone and the withdrawal of, the tamp apparatus, the bone tamp condensing the bone graft material in the voids.

16. The method of treating a bone fracture using a tamp apparatus of claim 12, wherein the step of treating the fracture includes treating cortical bone material and cancellous bone material.

17. A tamp apparatus for use in surgical operations for the realignment of fractured bone, the tamp apparatus comprises:
 a cannula that has a tubular wall that includes a distal end portion and a proximal end portion, the distal end portion includes a distal terminal end and a the proximal end portion includes a proximal terminal end;
 a lumen defined by the tubular wall of the cannula, the lumen extends from a first opening defined in the proximal terminal end to a second opening defined in the distal terminal end, the first opening can further include being adapted to couple with a source of bone graft material and the second opening can further include being configured for the injection of bone graft material, the first opening has a first diameter and the second opening has a second diameter, the diameter of the first opening is larger than the diameter of the second opening, the distal end portion of the cannula includes a distally directed taper of the inner wall of the tubular wall that defines the lumen, the taper of the inner tubular wall decreases the diameter of the second opening;
 a distally directed tamping face of the cannula adapted to displace bone from a fractured position to an approximately natural position, the tamping face defined by the distal terminal end of the distal end portion of cannula between an outside diameter of the tubular wall of distal terminal end and an outside diameter of the second opening, the distal taper of the inner surface of the tubular wall increases the surface of the tamping face;

a central longitudinal axis defined between the distal end portion and the proximal end portion of the cannula, the distal end portion includes a plurality of slots defined in the tubular wall and the slots define a plurality of elements, the elements movable between a first position wherein the elements are approximately aligned with the longitudinal axis and a second position where in the elements are oblique to the longitudinal axis, the slots extend from the distally directed tamping face proximally to a terminal end, the tamping face including a distal end of each element, the tubular wall includes a hinge in proximity to the terminal end of the slot for the movement of each element between the first position and the second position, the element in the second position moved about the hinge and outward from the central longitudinal axis;

a retention mechanism that includes the elements resisting rotation from the first position to the second position and biases the elements to the first position; and a stylet that extends between a distal end portion and a proximal end portion, the proximal end portion of the stylet includes a base, the distal end portion of the stylet includes a tamping face, the stylet insertable into the lumen of the cannula, the stylet approximately axially rigid and movable in the lumen, the stylet adapted to contact and displace the tapered portion of the tubular wall of the cannula and move the elements from the first position to the second position, the cannula and stylet connect together in the second position as a fixed assembly for tamping, a tamping face of the tamp apparatus defined by the distal ends of the elements in the second position and stylet distal end, the base adapted to receive an external force that drives the tamping faces of the stylet and elements.

18. The tamp apparatus of claim 17, wherein the second position fixes the relative positions of the cannula and the stylet, the second position structured to receive and transfer force along the longitudinal axis to the combined tamping face of the terminal ends of the cannula and stylet, in the second position the terminal ends of the cannula and the stylet define a contiguous tamping face, in the second position the terminal ends of the cannula and stylet are approximately flush.

19. The tamp apparatus of claim 17, wherein the stylet includes a tubular wall, the tubular wall of the stylet defines a fluid tight conduit, the stylet adapted to transfer bone graft material from an opening defined in the proximal end portion of the stylet to an opening defined in the distal end portion of the stylet.

20. The tamp apparatus of claim 17, wherein the retention mechanism assists in the retaining of the elements in the second position against the stylet.

21. The tamp apparatus of claim 17, wherein the stylet includes at least two stylets with differing diameters and the diameter of the stylet is selected to define a desired diameter of combined tamping face of the stylet and cannula in the second position.

22. The tamp apparatus of claim 17, wherein the stylet has a tubular wall and the tubular wall defines an aperture, the base of the stylet defines a proximal opening of the aperture that includes a connector adapted to interface with an external source of bone graft material and the distal end of the stylet defines a distal opening, the distal opening of the stylet adapted to inject the bone graft material.

23. The tamp apparatus of claim 17, wherein the tamp apparatus in the second position is adapted to displace cancellous bone and cortical bone.

\* \* \* \* \*